United States Patent
Ahluwalia et al.

(10) Patent No.: US 10,765,840 B2
(45) Date of Patent: *Sep. 8, 2020

(54) CONTENT INFLATION AND DELIVERY SYSTEM

(71) Applicants: Prabhat Kumar Ahluwalia, Little Falls, NY (US); Puja Ahluwalia, Little Falls, NY (US)

(72) Inventors: Prabhat Kumar Ahluwalia, Little Falls, NY (US); Puja Ahluwalia, Little Falls, NY (US)

(*) Notice: Subject to any disclaimer, the term of this patent is extended or adjusted under 35 U.S.C. 154(b) by 101 days.

This patent is subject to a terminal disclaimer.

(21) Appl. No.: 15/245,447

(22) Filed: Aug. 24, 2016

(65) Prior Publication Data

US 2016/0361522 A1 Dec. 15, 2016

Related U.S. Application Data

(63) Continuation of application No. 14/214,625, filed on Mar. 14, 2014, now Pat. No. 9,445,818.

(60) Provisional application No. 61/788,011, filed on Mar. 15, 2013, provisional application No. 61/787,901, filed on Mar. 15, 2013.

(51) Int. Cl.
| | |
|---|---|
| *A61B 17/12* | (2006.01) |
| *A61M 25/10* | (2013.01) |
| *A61B 17/02* | (2006.01) |
| *A61M 25/00* | (2006.01) |
| *A61M 39/10* | (2006.01) |

(Continued)

(52) U.S. Cl.
CPC ... *A61M 25/10184* (2013.11); *A61B 17/0218* (2013.01); *A61B 17/12022* (2013.01); *A61B 17/12136* (2013.01); *A61M 25/0017* (2013.01); *A61M 25/104* (2013.01); *A61M 25/1011* (2013.01); *A61M 25/10185* (2013.11); *A61M 39/10* (2013.01); *A61B 2017/00557* (2013.01); *A61B 2017/0225* (2013.01); *A61B 2017/1205* (2013.01); *A61B 2017/12054* (2013.01); *A61B 2017/12095* (2013.01); *A61F 5/003* (2013.01); *A61F 5/0036* (2013.01)

(58) Field of Classification Search
CPC .............. A61M 25/10; A61M 25/1018; A61M 25/10184; A61M 25/10185; A61M 2025/1054; A61B 17/0218; A61B 17/12022; A61B 17/12136; A61B 2017/12054; A61B 2017/12095; A61F 5/003; A61F 5/0036
USPC ........................................................ 606/192
See application file for complete search history.

(56) References Cited

U.S. PATENT DOCUMENTS

| | | | |
|---|---|---|---|
| 3,834,394 A * | 9/1974 | Hunter | A61B 17/12031 604/907 |
| 6,293,960 B1 * | 9/2001 | Ken | A61B 17/12113 606/195 |

(Continued)

FOREIGN PATENT DOCUMENTS

JP 2010-224709 * 10/2010 ............. A61B 5/224

*Primary Examiner* — Melanie R Tyson
(74) *Attorney, Agent, or Firm* — Pierson Intellectual Property LLC

(57) ABSTRACT

A content inflation and delivery system including a container including a fluid inlet in fluid communication with a fluid outlet; wherein the fluid outlet is positioned between the fluid inlet and a second end of the container. The system also includes an inflatable content being configured for inflation and delivery from the second end of the container.

20 Claims, 16 Drawing Sheets

(51) Int. Cl.
*A61F 5/00* (2006.01)
*A61B 17/00* (2006.01)

(56) References Cited

U.S. PATENT DOCUMENTS

| | | | |
|---|---|---|---|
| 9,445,818 B2* | 9/2016 | Ahluwalia | A61M 39/10 |
| 2002/0165572 A1* | 11/2002 | Saadat | A61B 17/12022 |
| | | | 606/194 |
| 2008/0033480 A1* | 2/2008 | Hardert | A61B 17/12136 |
| | | | 606/200 |
| 2010/0251837 A1* | 10/2010 | Bouasaysy | A61F 5/0036 |
| | | | 73/865.6 |
| 2013/0190656 A1* | 7/2013 | Toyota | A61B 5/224 |
| | | | 600/590 |
| 2014/0074142 A1* | 3/2014 | Khieu | A61F 5/003 |
| | | | 606/192 |

\* cited by examiner

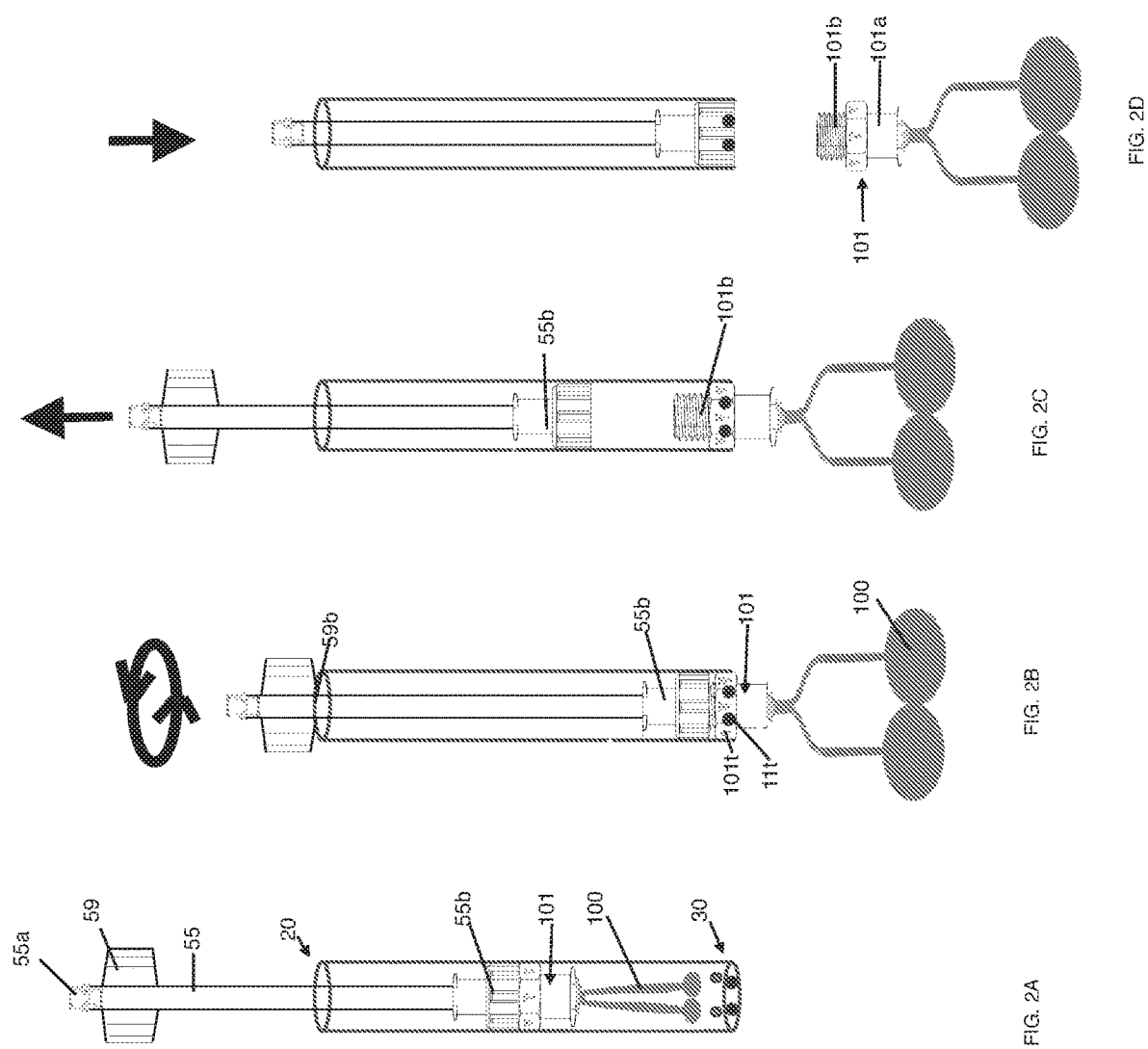

FIG. 3C
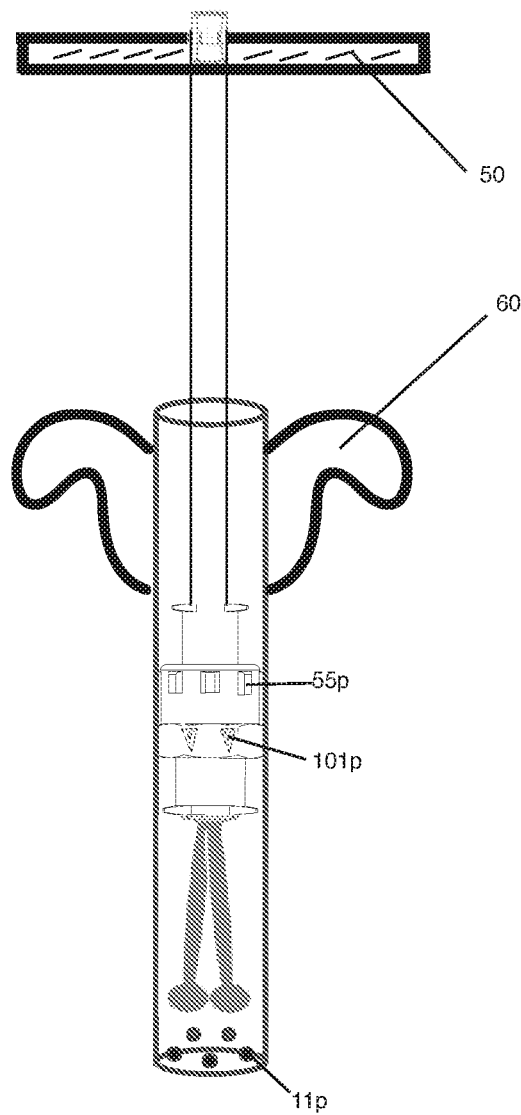
FIG. 3D
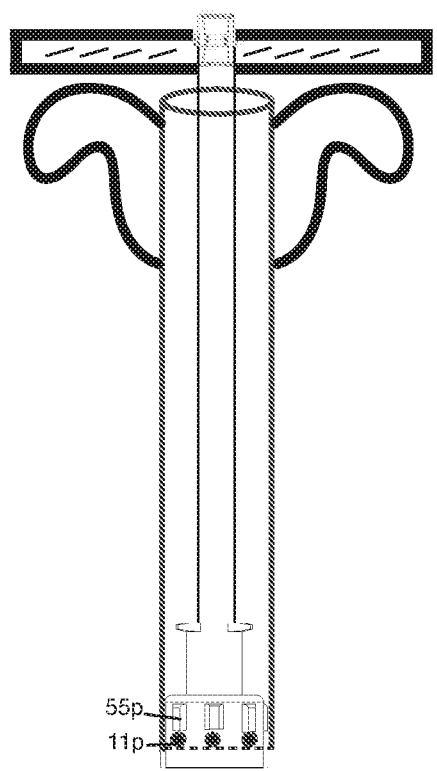
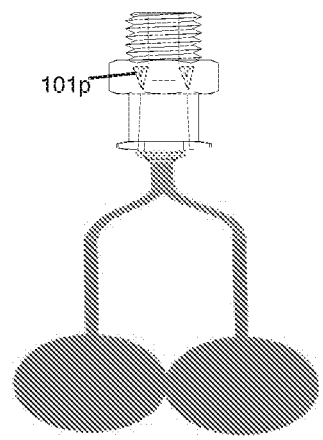

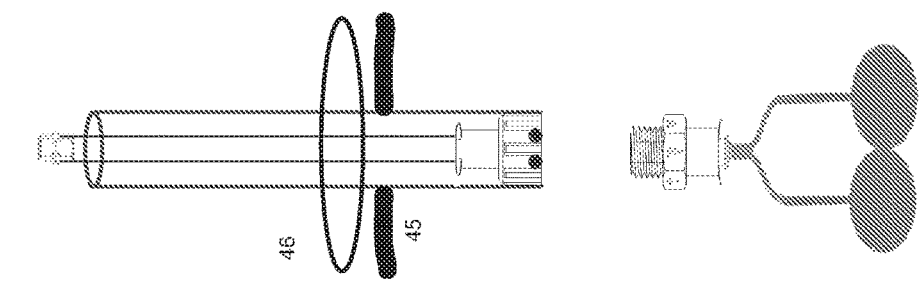
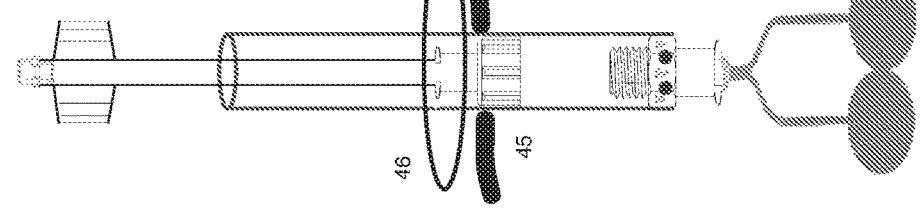
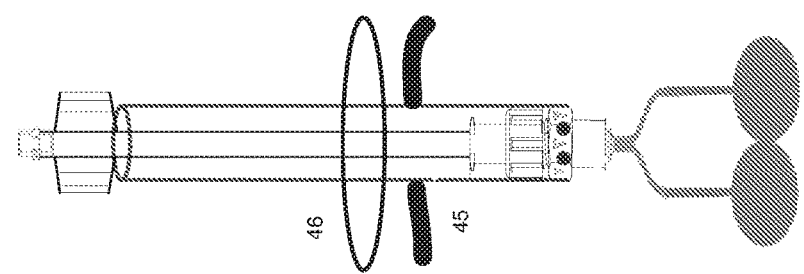
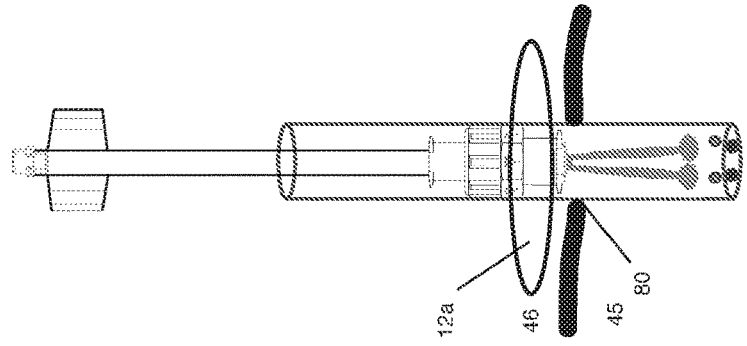

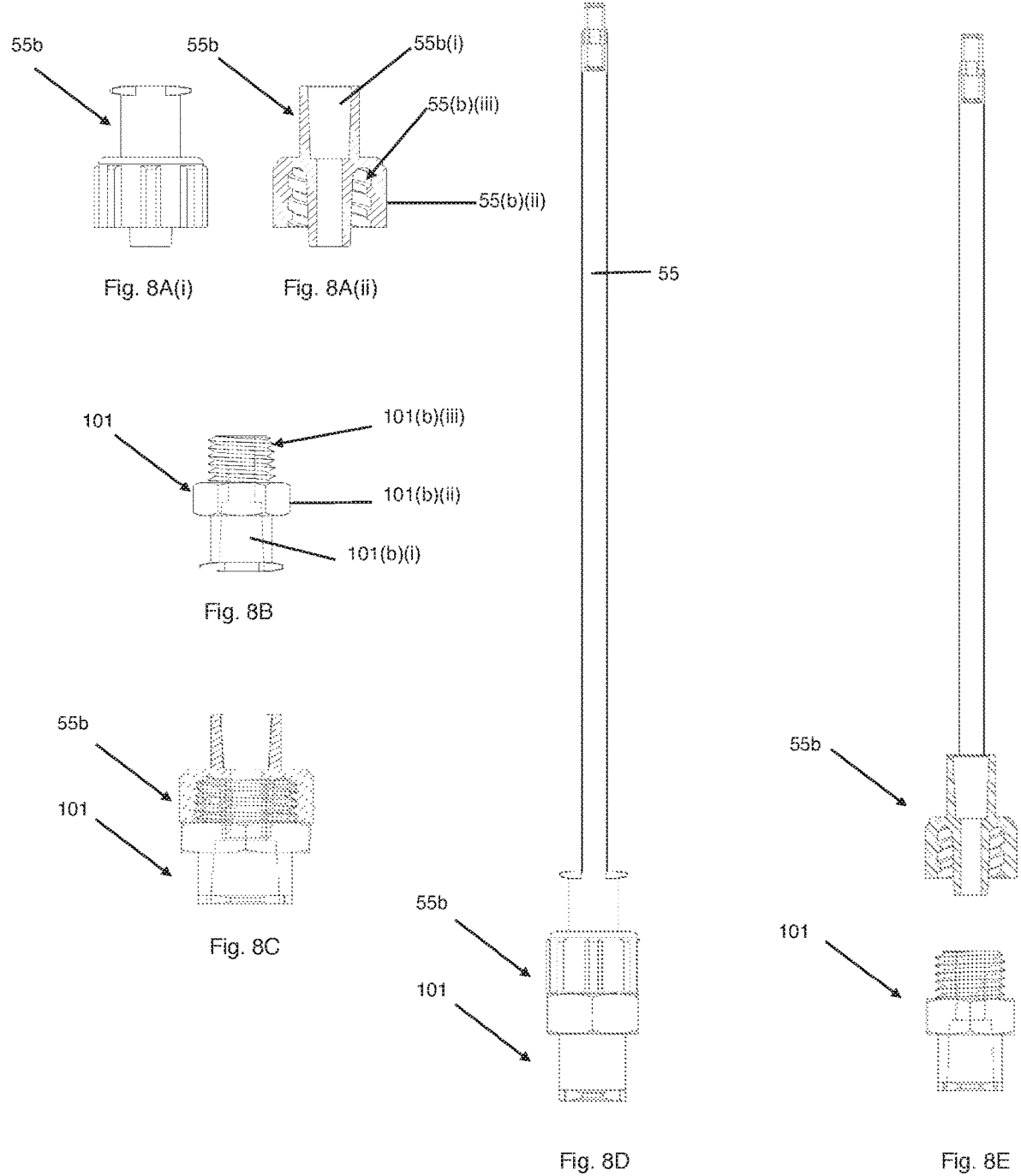

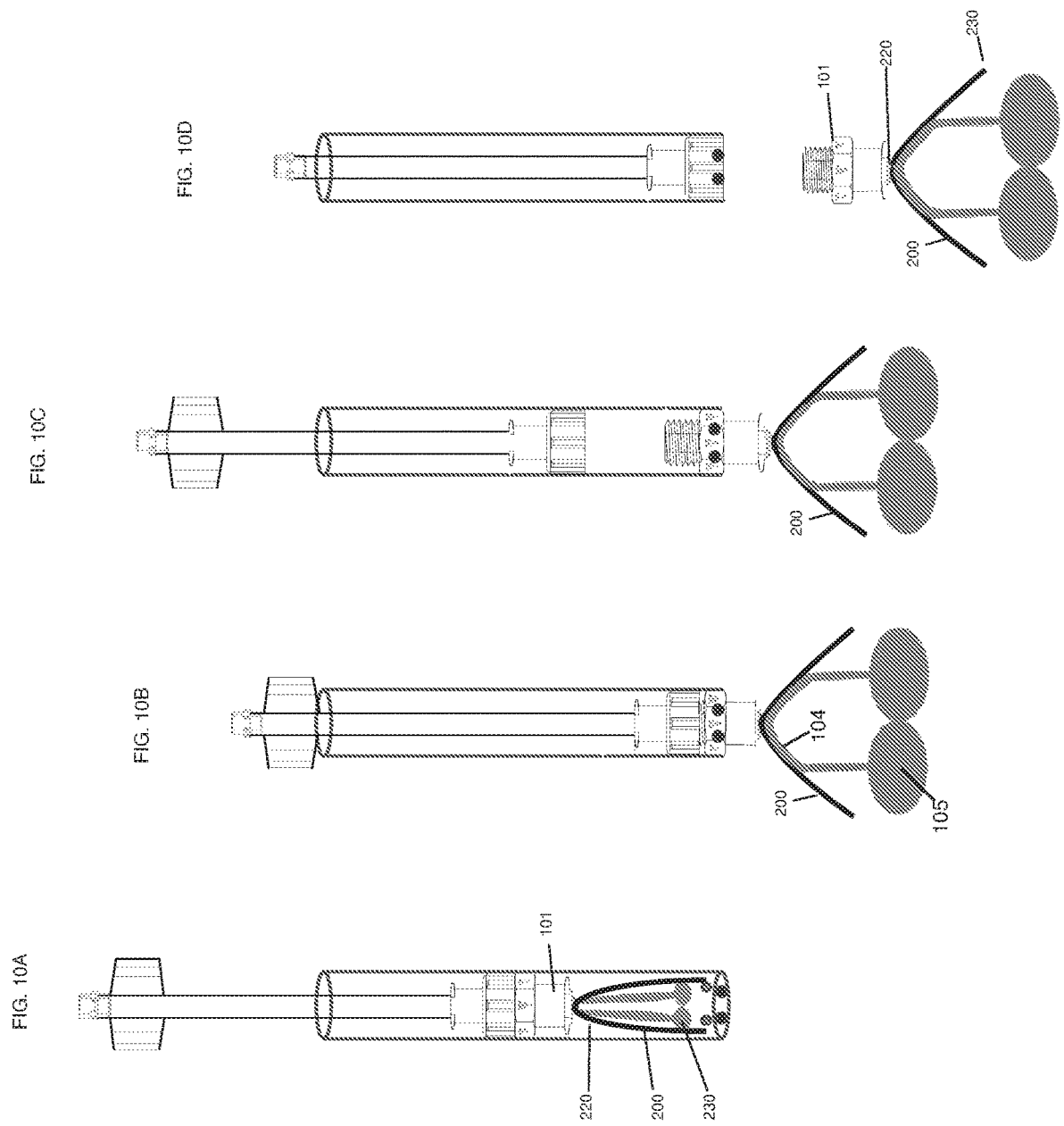

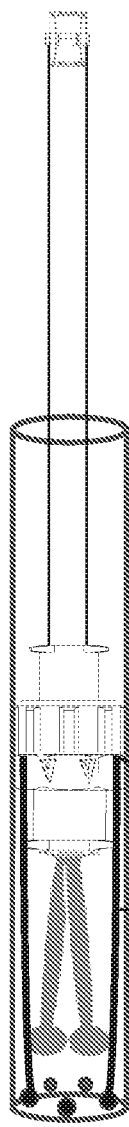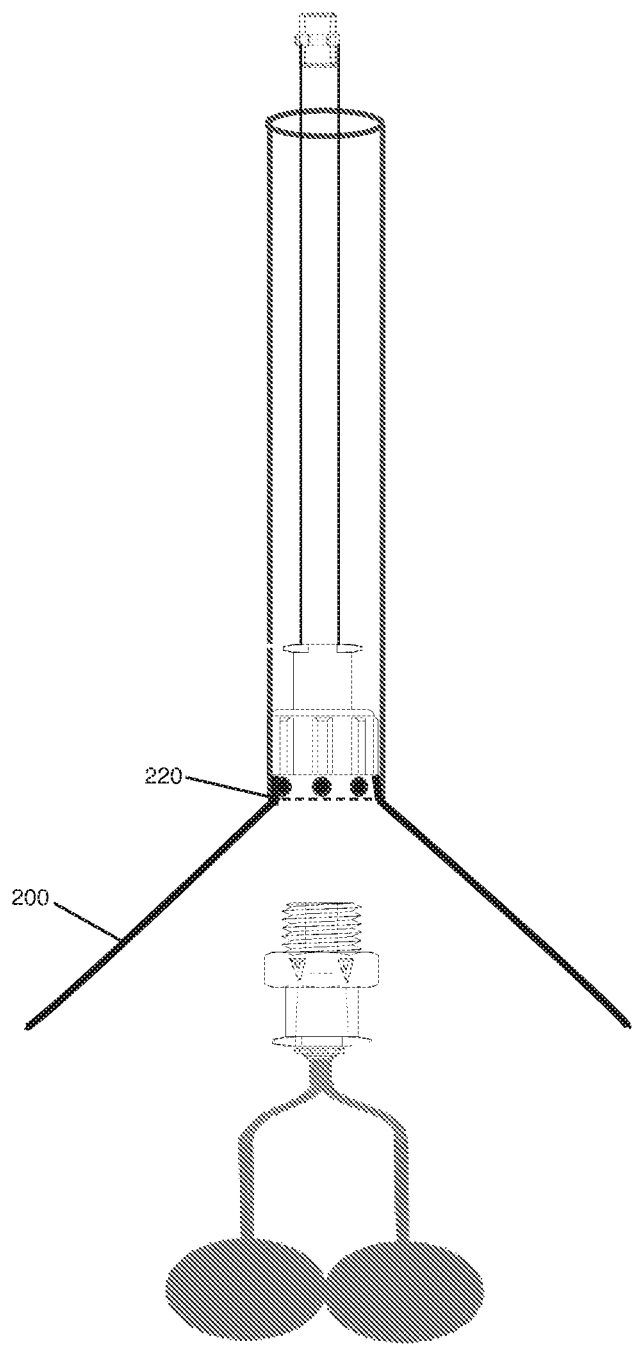
FIG. 11C
FIG. 11D

CONTENT INFLATION AND DELIVERY SYSTEM

CROSS-REFERENCE TO RELATED APPLICATIONS

This application claims a benefit of priority under 35 U.S.C. § 119 to Provisional Application No. 61/788,011 and Provisional Application No. 61/787,901 filed Mar. 15, 2013, which is fully incorporated herein by reference in its entirety. Additionally, this application is a continuation of U.S. Ser. No. 14/214,625 filed on Mar. 14, 2014. This application incorporates by reference in its entirety U.S. patent application Ser. No. 13/432,960.

BACKGROUND INFORMATION

Field of the Disclosure

Examples of the present disclosure are related to delivery systems and methods for inflatable content that requires delivery through a lumen or container. Specifically, embodiments are related to devices and tools that reduce, minimize, and/or lessen the invasiveness of delivery, including but not limited to medical procedures.

Background

Certain procedures require content inflation and delivery by a lumen or container. This includes medical or surgical procedures associated with inflatable or expandable devices, implants, or tools, such as for example, catheters or devices with balloon component(s) that require inflation by air or fluid (hereinafter "fluid").

Conventional delivery systems are ill equipped to efficiently and precisely inject, expand, fill, or inflate (hereinafter "inflate") such inflatable content, such as devices, implants or tools, in a non-invasive manner.

Accordingly, a need exists for easy and effective content and inflation delivery systems and methods.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIGS. 2A-2D show inflation and delivery of content using an embodiment.

FIGS. 3A-3D show embodiments configured to limit, reduce, or prevent release of an outlet from a surgical inflation and delivery system, in addition to handle components.

FIG. 4A-4D show inflation and delivery of content in an embodiment in a surgical setting.

FIGS. 8A-8E show an embodiment of an outlet configured for coupling to an inlet.

FIGS. 10A-10D show inflation and delivery of content in an embodiment including one or more prongs.

FIGS. 11C-11D show an embodiment where prongs are coupled to the outlet.

Figure 1:
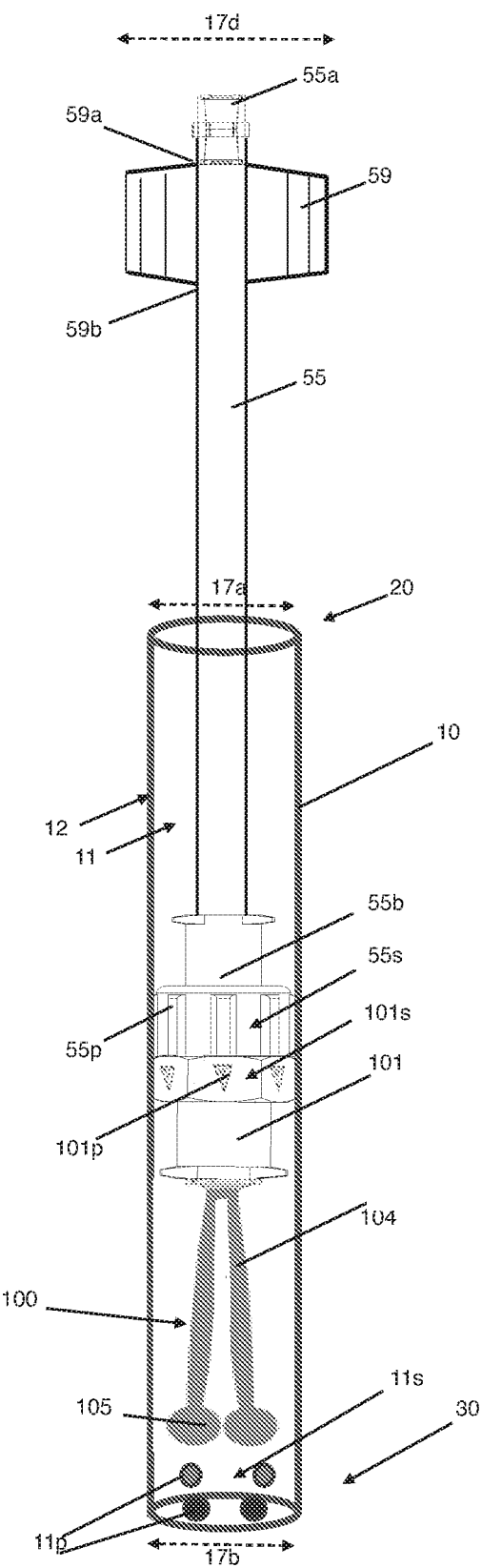
FIG. 1 shows an embodiment of a surgical inflation and delivery system.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

In the following description, numerous specific details are set forth in order to provide a thorough understanding of the present embodiments. It will be apparent to one having ordinary skill in the art, that the specific detail need not be employed to practice the present embodiments. In other instances, well-known materials or methods have not been described in detail in order to avoid obscuring the present embodiments.

FIG. 1 shows an embodiment of a surgical inflation and delivery system 1000 (hereinafter "System 1000"). FIG. 1 shows a container 10 comprising a compartment, delivery tube, or lumen with an inner surface 11 and outer surface 12 extending from a first end 20 to a second end 30. The first end 20 has a diameter 17a, and the second end has a diameter 17b. First end 20 is configured to receive a hollow shaft 55. The hollow shaft 55 is configured to receive fluid at an inlet 55a and to deliver a fluid at an outlet 55b. Outlet 55b is positioned between the first and second end of the container and is in fluid communication with an inlet 101 of contents 100, which are also positioned between the first end 20 and second end 30. Thus, when inlet 55a receives a fluid via a syringe, saline bag or other fluid source, the fluid travels through the hollow shaft 55, is delivered out of outlet 55b and into inlet 101 to inflate contents 100.

Additionally, FIG. 1 shows a hook, clamp or clip (hereinafter "clip 59") coupled to shaft 55 and located proximal to the first end 20. Clip 59 may have a first point of attachment 59a to the shaft (hereinafter "point 59a") and a second point of attachment 59b (hereinafter "point 59b"), wherein point 59b is positioned between the first point 59a and the first end 20 of container 10. Clip 59 may be configured to partially or completely encase shaft 55. Responsive to clip 59 partially or completely encasing shaft 55, point 59b may be positioned adjacent to first end 20. The diameter 17d of clip 59 exceeds the diameter 17a of first end 20. Thus, clip 59s, reduces, or prevents the hollow shaft 55 from sliding, moving, or translating beyond point 59b into the first end 20 of the container 10. In other words, when clip 59 is coupled to the shaft 55, the portion of the shaft 55 between point 59b and the proximal end of shaft 55 remains outside or proximal to container 10. Or, when inlet 55a is at the proximal tip of shaft 55, the distance between point 59b and the proximal end of shaft 55 remains outside or proximal to container 10. Other configurations designed to prevent release of outlet 55b are described below and include but are not limited to use of a bag, protrusions, an inner rail, or disc.

Figure 12A:
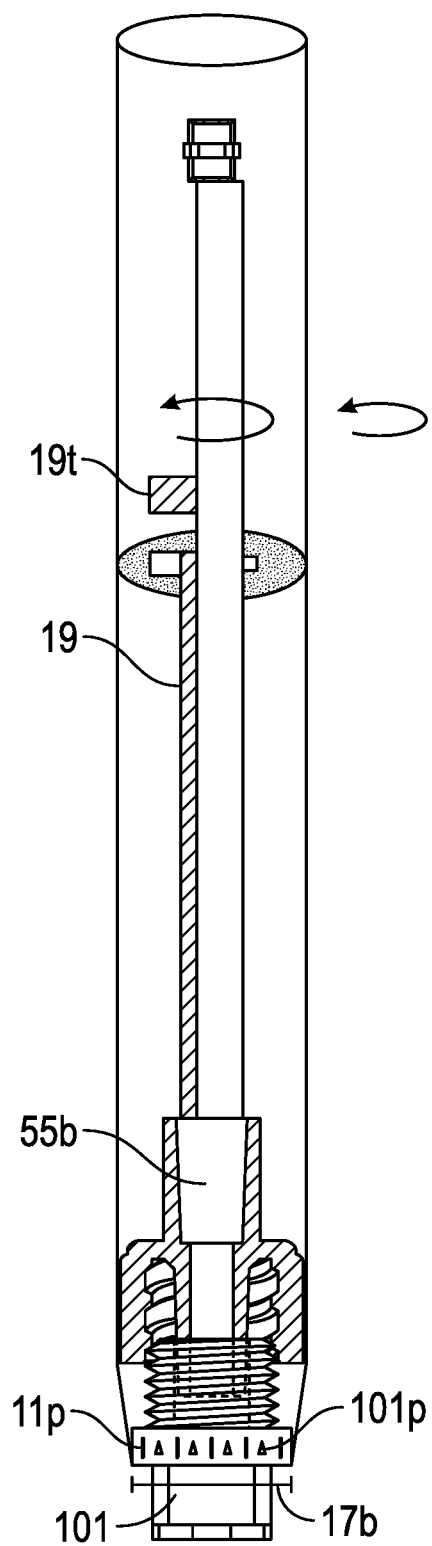
FIG. 12A-C show an embodiment including a rail and disk.

Alternatively, the second end 30 may designed with a diameter less than the diameter of the first end and the outlet 55b, but having a diameter equal to or greater than the diameter of inlet 101. A narrowed second end 30 diameter has the additional benefit of limiting, reducing, or preventing the outlet 55b from exiting the second end, as illustrated in FIG. 12A.

Additionally, FIG. 1 shows multiple raised surfaces in system 1000. Surface 11s is positioned between the first end 20 and second end 30. Surface 11s may include one or more protrusion(s), bump(s), dot(s), abutment(s), shelve(s), ledge(s), ridge(s) or tab(s) (hereinafter "container protrusion 11p") on the inner surface 11 of the container. In FIG. 1, container protrusion 11p has a circular shape for illustrative purposes. Surface 101s is positioned on the outer surface of inlet 101, and surface 101s may include one or more protrusion(s), bump(s), dot(s), abutment(s), shelve(s), ledge(s), ridge(s) or tab(s) (hereinafter "content inlet protrusion 101p") on the outer surface of inlet 101. In FIG. 1, content inlet protrusion 101p has a triangular shape for illustrative purposes. Surface 55s is positioned on the outer surface of outlet 55b and may include one or more protrusion(s), bump(s), dot(s), abutment(s), shelve(s), ledge(s), ridge(s) or tab(s) (hereinafter "outlet protrusion 55p"). In FIG. 1, outlet protrusion 55p has a rectangular shape. It will be appreciated that the shapes and/or sizes of the elements shown in system 1000 may vary, such as container protrusion(s) 11p, content inlet protrusion(s) 101p, and outlet protrusion(s) 55p. The shapes illustrated are for illustrative purposes and may be interchanged or substituted with alternative shapes, as shown in FIGS. 7A-7D and further described below.

FIG. 1 also shows an embodiment of content 100, wherein the content includes a balloon 105 connected by a lumen or hollow elongated member 104, to another balloon, with an inlet for inflation (hereinafter "content inlet 101"). The elongated member 104, balloons 105, and inlet 101 form a "Y shape" with the inlet 101 at the base portion of the "Y." In other embodiments the lumen and balloons may form a "V" or "U" shape. In embodiments including more than two balloons, the elongated member may form more complex shapes, such as for example a "W".

Embodiments of Content 100 may include a plurality of balloons 105 and a plurality of inlets 101. Other embodiments may include a single balloon 105 and a single inlet 101, which may or may not be connected by a hollow lumen or elongated member 104. In other words, content 100 may include one or more balloons, or one or more balloon components.

Balloons 105 may be seamed balloons, or welded with heat. They may, among other embodiments, be pleated, pillowed, a paddle shaped, foldable or ultra-thin. In a surgical setting, the balloons may be configured to hold 0-100 ml, 100 ml-200 ml, 200 ml-300 ml, 300 ml-400 ml, 400-500 ml, 500-600 ml, or more than 600 ml for particularly large patients. The balloon(s) may have varying odometers and burst pressures and be configured for a heat-shrunk tubing or other commercially available tubing. For example, in a minimally invasive context the compliance range may be 0-15%, the balloons may transmit light over a broad spectrum including ND, the sizes may range from 0.5 to 50 mm, and the burst pressures may range from 5 to 500 PSI.

In other embodiments, content 100 may include any device configured to be inflated, such as catheter, of inflatable devices such as the organ retractor described in U.S. Pat. App. Publication No. 2012/13/432,960, which is incorporated by reference.

FIGS. 2A-2D show inflation and delivery of content 100 in an embodiment where content 100 requires inflation outside of the container 10. FIG. 2A shows a first configuration of system 1000 wherein content 100 is in a first position, wherein the first position may occur before delivery of content 100. FIG. 2B shows a second configuration where content 100 is partially or completely distal to the second end 30 and ready for inflation. FIG. 2C shows release of content inlet 101 and content 100 from outlet 55b. FIG. 2D shows release of content 100 from the system 1000.

FIG. 2A shows a first configuration, wherein system 1000 includes content 100 disposed within container 10 between the first end 20 and second end 30. Content 100 is affixed to a content inlet 101, which in turn is coupled to outlet 55b and hollow shaft 55. Shaft inlet 55a is proximal to the first end 20. The proximal portion of hollow shaft 55 is coupled to a detachable clip 59, which limits, reduces, and/or prevents the shaft inlet 55a from sliding into the first end of container 10. In embodiments, when inflation of content 100 would result in an expanded content diameter 17c being less than the container diameter 17b, fluid may be delivered into inlet 55a, and the contents may be inflated in the first position, prior to release. However, in embodiments when inflation of content 100 would result in an expanded content diameter 17c being greater than or equal to diameter 17b, fluid may be delivered after the content 100 is delivered outside of or distal to second end 30 of container 10.

FIG. 2B shows a second configuration wherein hollow shaft 55 has been pressed into a second position and the content 100 has been delivered outside of or distal to the second end 30 of container 10. In the second position, clip 59 limits, reduces, or prevents movement of translation of the hollow shaft 55 beyond point 59b into the first end 20 of container 10. Specifically, point 59b is proximal to or in contact with the first end 20 of container 10. Although a portion of content inlet 101 may be delivered outside of or distal to the second end 30 of container 10, content inlet protrusion 101p remains within container 10, or proximal to second end 30 of container. Specifically, content inlet protrusion 101p may interface with container protrusion 11p, such that content inlet protrusion 101p and container protrusion 11p are positioned adjacent to each other or in contact with each other. In embodiments, responsive to content inlet protrusion 101p interfacing with container protrusion 11p, other content inlet protrusions 101p may be interfaced with corresponding container protrusions 11p. When content inlet protrusion(s) 101p and container protrusion(s) 11p are interfaced, a rotation of outlet 55b (for example, via rotation of the connecting shaft 55) would cause the container protrusion(s) 11p to hit, collide, abut, or contact content inlet protrusion(s) 101p, such that rotation of inlet 101 is limited, prohibited, or eliminated. In embodiments, content inlet protrusions 101p and container protrusions 11p may be positioned at offsetting even or uneven intervals, such that content inlet protrusions 101p may slide or be placed between two container protrusions 11p.

Clip 59 may be positioned so that when outlet 55b is assembled or coupled to content inlet 101, the distance between point 59b and the distal end of outlet 55b enables content inlet protrusion(s) 101p to align, slide into, or be adjacent to container protrusion(s) 11p. In other words, clip 59's placement limits, reduces, or prevents the shaft 55 and attached outlet 55b and inlet 101 from moving beyond the second end 30, and may be configured to ensure the alignment of content inlet protrusion 101p and container protrusion 11p. If the clip is uncoupled, the shaft 55 and any attached components, such as outlet 55b, may fall out of the delivery system and, in a surgical setting, into the patient.

In the configuration illustrated in FIG. 2B, content 100, which is distal to the second end 30, may be inflated. A screw portion 101b of content inlet 101 may screw into outlet 55b, thereby limiting, inhibiting, or preventing content 100 from releasing during inflation. This is particularly important if content 100 requires significant inflation of fluid, such as water or saline.

After inflation, outlet 55b may be uncoupled from inlet 101 to release inflated content 100. FIG. 2B shows an embodiment wherein content inlet 101 is coupled to outlet 55b via a screw portion 101b. Thus, uncoupling may be achieved by rotating clip 59 (or alternatively inlet 55a or hollow shaft 55) to rotate or unscrew outlet 55b from content inlet 101. As outlet 55b rotates, one or more content inlet protrusion 101p and one or more container protrusion 11p interface, contact, collide or lock into one another, limiting, inhibiting, or preventing rotation of inlet 101. In other words, inlet 101 is fixed or locked into position by the interlocking of content inlet protrusion(s) 101p to container protrusion(s) 11p. In particular, one or more protrusions 101p collide with one or more protrusions 11p, lock into a fixed position and thereby limit, reduce, or prevent 101 from rotating with outlet 55b. The locked position of inlet 101, facilitated by content inlet protrusion 101p and container protrusion 11p, enables a practitioner to unscrew outlet 55b from content inlet 101 when, for example, the two components are configured as complementary male and female lure screw portions.

The raised surfaces and/or protrusions may be configured to limit, prevent, or reduce rotation along the horizontal axis, but allow movement along the vertical axis (wherein the vertical axis extends from the first end 20 to the second end 30, and the horizontal axis is perpendicular to the vertical axis). Thus, in the embodiment above, vertical movement or translation of inlet 101 is not limited, reduced, or prevented by the container protrusion 11p and content inlet protrusion 101p, but is instead limited, or reduced, prevented by clip 59.

FIG. 2C shows a third configuration, wherein the outlet 55b of system 1000 is uncoupled from the inlet 101 of content 100. In this configuration, gravity may exert a sufficient force to pull and release inlet 101 from the second end 30. Alternatively, the gravitational force may not be large enough, or container protrusion 11p and content inlet protrusion 101p may limit a gravitation release. In either scenario, a practitioner may pull the hollow shaft from the second end toward the first end, remove clip 59 (if attached) and push the hollow shaft toward the second end 30 with sufficient force so outlet 55b bumps, hits, collides, knocks against inlet 101. The application of force of outlet 55b against inlet 101 pushes the inlet 101 through and out the second end 30 of the container 10 to facilitate a release of contents 100 from the system 1000. When outlet 55b and inlet 101 are configured for coupling via a screwing mechanism, outlet 55b does not reattach to inlet 101 upon impact because coupling requires screwing inlet 101a into outlet 55b FIG. 2D shows a fourth configuration wherein contents 100 and inlet 101 are released and separated from the delivery system 1000 and the outlet 55b is located at the second end.

FIGS. 3A-3D show embodiments configured to limit, reduce, or prevent release of outlet 55b from the system 1000. In this embodiment, outlet 55b may include one or more outlet protrusion(s) 55p located on its outer surface 55s and along the same vertical axis as container protrusion 11p. In this embodiment, when outlet 55b moves from the first end 20 towards the second end 30, outlet protrusion 55 bumps, collides, contacts or locks into a container protrusion located on the inner surface 11s at point 59c. In particular, container protrusion 11p may bump, collide, contact or lock into one or more outlet protrusion(s) 55p to limit, reduce, or prevent vertical translation or movement of outlet 55b beyond the point of contact at point 59c.

Figure 3A:
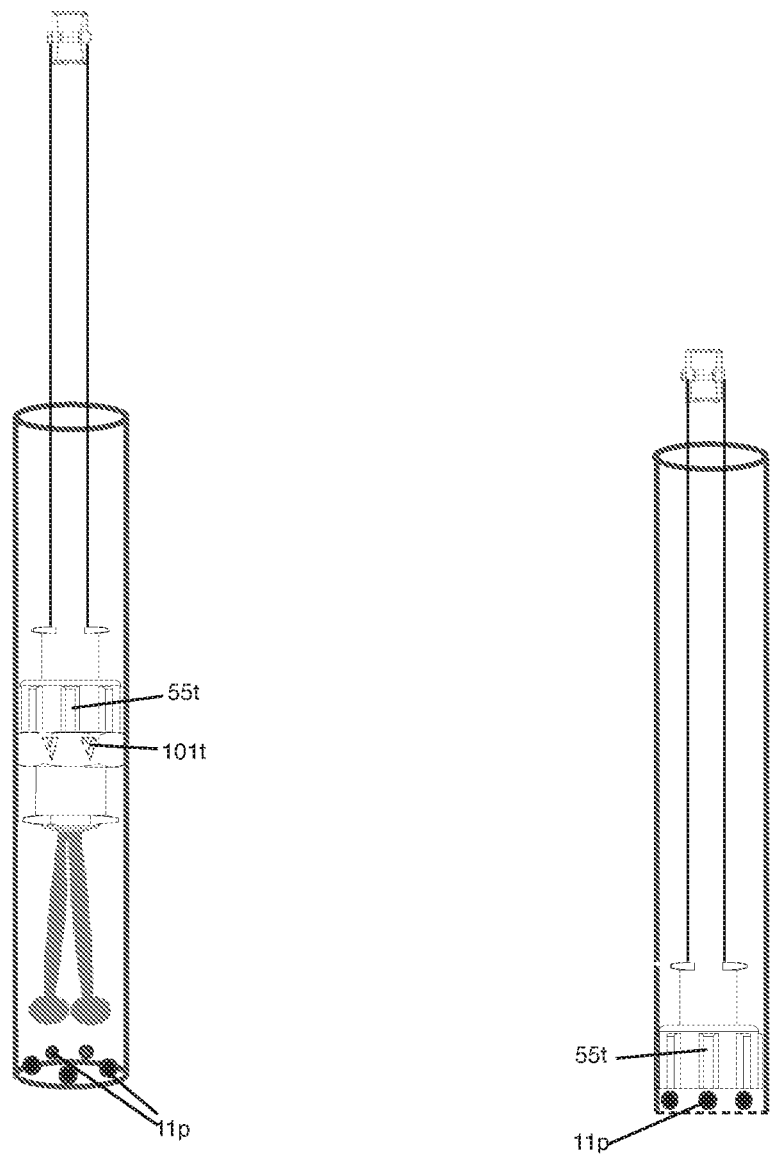
Figure 3B:
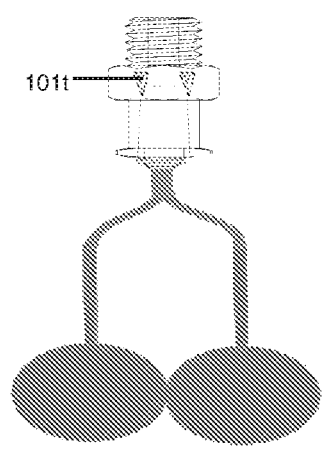

Outlet surface 55s may include one or more protrusion(s) 55p located at the distal portion of outlet 55b, as shown in FIGS. 3A & 3B, but this limits, reduces, prevents the outlet 55b from pushing or knocking out inlet 101 in the third configuration described above. Alternatively, outlet surface 55s may include one or more container protrusion(s) 55p located at a middle or proximal portion of outlet 55b, as shown in FIGS. 3C & 3D. In this configuration, sufficient vertical translation is enabled to knock out or displace outlet 101 from the system 1000.

FIGS. 3A-3D also shows embodiments wherein one or more outlet protrusion(s) 55p may substitute use of clip 59 altogether. However, when one or more outlet protrusion(s) 55p are located at the distal portion of outlet 55b, as shown in FIG. 3B, a practitioner is limited or prevented from employing outlet 55b from pushing or knocking out inlet 101 from the second end 30, as described above. Alternatively, when one or more outlet protrusion(s) 55p are located at a middle or proximal portion of outlet 55b, as shown in FIG. 3D, a practitioner may blindly adjust the vertical translation or movement of hollow shaft 55 to achieve the desired horizontal alignment of one or more outlet protrusion(s) 55p and content inlet protrusion(s) 101p in preparation for unscrewing outlet 55b from inlet 101a. Thus, use of a clip 59 to limit vertical translation of the outlet 55b may be the preferred embodiment.

FIGS. 3B & 3C also shows that a hollow shaft 55 may be configured with a handle 50, wherein handle 50 may be configured to facilitate application of pressure upon the hollow shaft 55. The handle 50 may be positioned outside of the body of container 10 allowing a practitioner to grip, hold, and/or interface with handle 50. Handle 50 may be configured to receive a person's hand such that the person may apply pressure to handle 50 to displace outlet 55b or content 100 along the inner lumen of container 10, for example away from the first end 20 and towards the second end 30. Additionally, shaft inlet 55a may be configured at the proximal portion of the handle to facilitate injection of fluid. In an embodiment, first inlet 55a may receive fluid, which travels through shaft 55, outlet 55b and into inlet 101 for inflation of content 100.

FIGS. 3B and 3C also show that a second handle 60 may be located upon the outer surface 12 of container 10 to facilitate positioning and stabilization of the container 10. This is particularly useful when applying force upon the shaft 55; a practitioner may grip second handle 60 with one hand and apply force upon hollow shaft 55 with the other hand.

Configurations described in FIGS. 4A through 4D also show positioning of system 1000 in a minimally invasive surgery. For example, the first configuration (FIG. 2A) may be a starting position before the system 1000 is inserted into the patient via an incision, aperture, or a surgical port 80. After inserted into a port 80 (FIG. 2B), the distal end 30 is within the patient's interior 45 while the proximal end 20 remains on the patient exterior 46 allowing for inflation of content 100. Outlet 55b may be uncoupled from content inlet 101 (FIG. 2C), while portions of container 10 may be positioned within patient's interior 45 while portions of container 10 may be positioned outside of patient's interior 45. Container 10 may slide into and outside of the port to achieve any desired configuration. After release of content 100 in the fourth configuration (FIG. 2D), System 1000 may be removed from port 80, while content 100 may remain within patient's interior 45.

FIG. 4A-4D show that a System 1000 may also include one or more projections or protrusions (referred to hereinafter collectively and individually as "projection 12a"). Projection 12a may extend at an angle or orthogonally from outer surface 12 of container 10 and may have any shaped perimeter, including a circular, oval trapezoidal, polygonal or any mixed shape perimeter. Projection 12a may be slidable or slide along the outer surface 12 or may be integral to outer surface 12. Projection 12a may include an inner circumference that is configured to be positioned adjacent to outer surface 12 of container 10, and the under surface 12c of projection 12a may be configured to be positioned adjacent to a patient's body 45 or surgical port. Projection 12a may be configured to interface with an incision or port 80 to limit the movement, slippage or sliding of container 10. If projection 12a is interfaced with the port or patient, the portion of container 10 proximal to projection 12a may be prevented from sliding into the interior of a patient.

Figure 5:
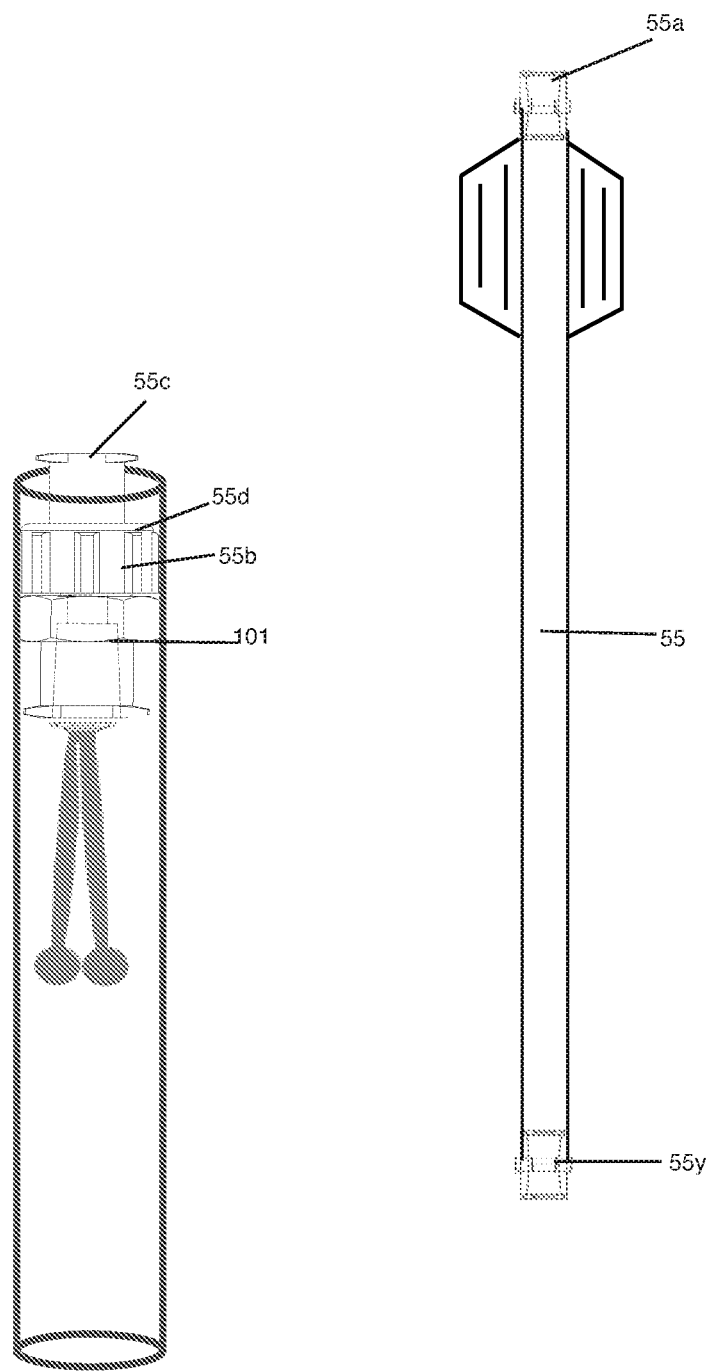
FIG. 5 shows an embodiment wherein a shaft is detachable from an outlet.

FIG. 5 shows an embodiment wherein shaft 55 is detachable from outlet 55b. Hollow shaft 55 is substituted by an inlet 55c configured for receiving fluid from an external source. Outlet 55b is coupled to an inlet 55c, located between outlet 55b and the first end 20, or proximal to the first end 20, as shown in FIG. 4. Inlet 55c is in fluid communication with outlet 55b, and may be configured to form part of the outlet 55b as a single unit, such as for example a dual female and male luer lock. Alternatively, inlet 55c and outlet 55b may be separate components coupled together.

Shaft 55 may instead be configured with a first end 55a and a second end 55y, and second end 55y may be configured to couple to inlet 55c. In this configuration, fluid is received at inlet 55a, travels through the hollow shaft 55, leaves outlet 55y and travels into inlet 55c.

In another embodiment, a hollow shaft 55 need not be employed. Instead, a stick or shaft 56 (which may or may not be hollow) may be employed to apply pressure to the inlet 55c to translate the outlet 55b through container, for example from the first end 20 to the second end 30. Alternatively, inlet 55c or outlet 55b may be comprised of an outer surface 55d facing or open to the first end 20. A stick or shaft 56 (which may or may not be hollow) may be employed to apply pressure upon outer surface 55 to translate the outlet 55b, content inlet 101 and coupled content 100 toward the second end. In either embodiment, fluid may be inserted in inlet 55c via other means, such as a syringe IV or connecting tube once the desired displacement is achieved.

Figure 6C:
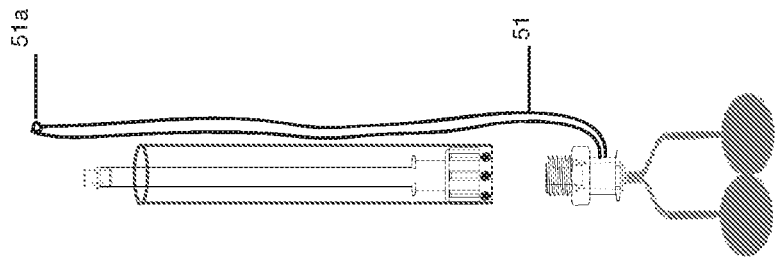
FIG. 6C shows an embodiment where a lumen may pass outside of a surface of a container.
Figure 6B:
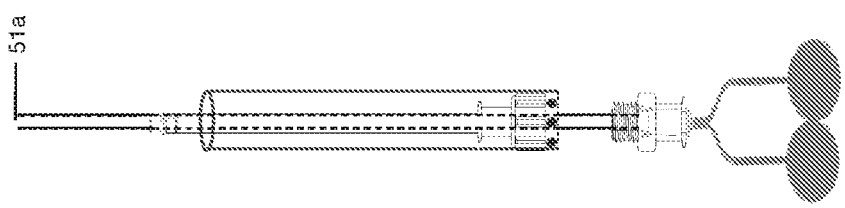
FIG. 6B shows an embodiment where an inner lumen may extend beyond or proximal to a shaft inlet and have a separate inlet.
Figure 6A:
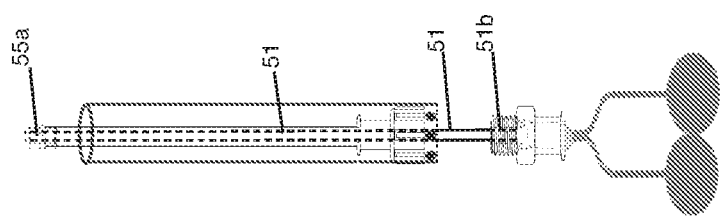
FIG. 6A shown an embodiment where an inner lumen may pass between the walls of a shaft and share an inlet with the shaft.

FIGS. 6A-6C shows an embodiment wherein content inlet 101 remains attached to an inner lumen 51 after delivery and deployment. Lumen 51 may include an inlet 51a positioned on a first end of lumen 51, an outlet 51b positioned on a second end of lumen 51, and a diameter smaller than the diameter of outlet 55b. Outlet 51b is configured for attachment or coupling to content inlet 101 or content 100. Inlet 51a of lumen 51 may have various configurations. In one embodiment, a portion of the inner lumen may couple to or be integral to hollow shaft 55, wherein the inlet 51a may be the same component as inlet 55a. Alternatively, as shown in FIG. 6A, the inner lumen 51 may pass between the walls of the shaft and share an inlet 55a with shaft 55. As shown in FIG. 6B, inner lumen 51 may extend beyond or proximal to shaft inlet 55a and have a separate inlet 51a. Alternatively, the lumen may not pass through shaft 55, but pass between the inner surface 11 of container 10, adjacent to the outlet 55b, or through a separate outlet located on outlet 55b. Alternatively, lumen 51 may pass outside the surface of container 10 (as shown in FIG. 6C). In any of the above-described configurations, lumen 51 affixes to inlet 101 via outlet end 51b and enables delivery of fluid via inlet 51a.

An extended lumen 51 enables a practitioner to retain a lumen connection to the contents 100 for manipulation, additional inflation, or retrieval during surgery. A medical practitioner may seek to inject or inflate additional fluid into content 100, which content is within the patient.

FIGS. 7A-7D illustrate various configurations of protrusion(s) 11p and protrusion(s) 101p with respect to their respective surfaces 11s and 101s and with respect to each other, from a top-down perspective. FIGS. 7A-7D may also illustrate various configuration of protrusion(s) 55p and protrusion(s) 11p with respect to their respective surfaces 55s and 101s and with respect to each other (wherein the 101 components may simply be substituted for 55 components). However, if protrusion(s) 55p are intended to prevent the release of outlet 55b (as described above), at least one protrusion 55p must overlap at least one protrusion 11p from a top-down perspective.

Figure 7A:
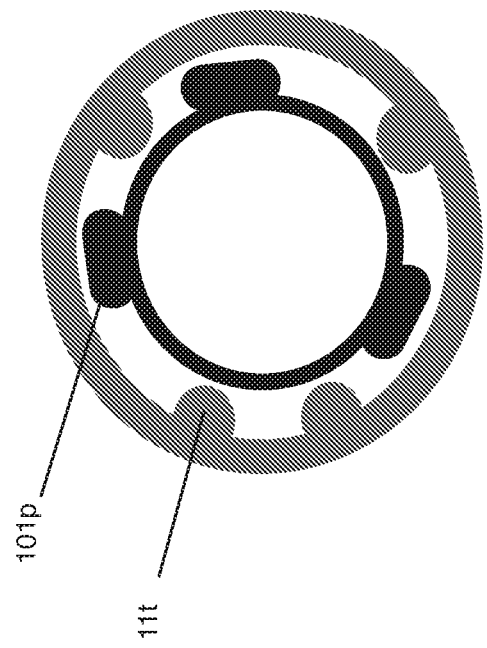
FIGS. 7A-7D show embodiments of various configurations of protrusions with respect to their respective surfaces.
Figure 7B:
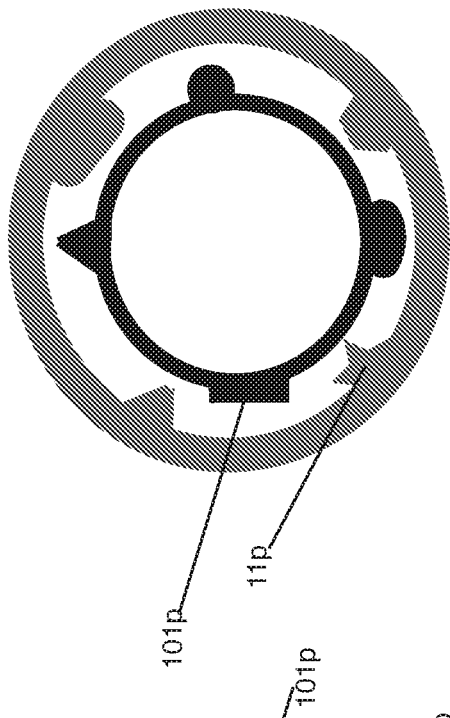
Figure 7C:
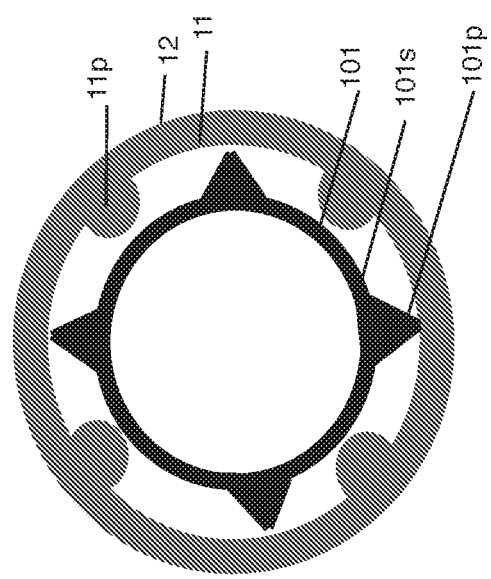
Figure 7D:
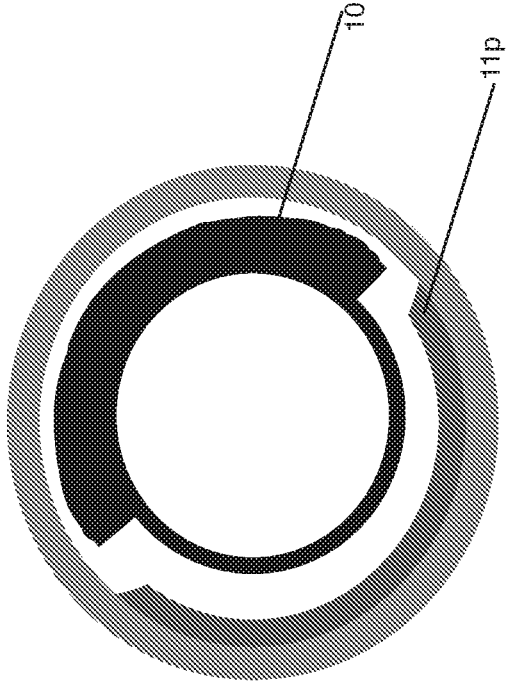

Protrusion(s) 11p, protrusion(s) 101p, and protrusions 55(p) may be evenly spaced (e.g., FIG. 7A) or unevenly spaced (e.g., FIG. 7B). They may be polygonal, curved, square, trapezoidal, mixed shape or any shape, which facilitates a locking, interfacing, or coupling function. Protrusion(s) 11p, 101p and 55p may share the same shape (e.g., FIG. 7C), differ in shape (e.g., FIG. 7B), or have a mixed configuration of shapes within their respective sets (e.g., FIG. 7D). For example, protrusions 11p may consist of a single oval shapes protrusion, a single triangle shaped protrusion, and a polygonal shaped protrusion (all unevenly spaced) whereas protrusions 101 may consist of a series of evenly shaped circular protrusions, or vice-versa. The protrusions may be smooth, jagged or mixed. They may be continuous or discontinuous along the same horizontal axis, dispersed in multiple rows, or dispersed generally, with a pattern or without a pattern. Protrusion(s) 11p, 101p or 55p may be angled with respect to their surfaces 11s, 101s and 55s, respectively. Protrusion(s) 11p, 101p and 55p may include additional protrusions at an angle or orthogonal to the protrusion to facilitate a locking function. The protrusions may have varying thickness, different thicknesses or the same thickness. Additionally, surfaces 11s, 101s and 55s need not all include protrusions. For example, surfaces 11s and 101s may include protrusions but surface 55s may not include protrusions. Alternatively, surfaces 11s and 55s may include protrusions but surface 101s may not include protrusions.

FIGS. 8A-8E show an embodiment of outlet 55b configured for coupling to inlet 101. FIG. 8A(i) shows an embodiment of an outlet 55b configured as a male luer component and FIG. 8A(ii) shows a cross-sectional view of the same component. The white space in the cross-section shows a hollow channel or inner tubular portion 55(b)(i) configured for the passage of fluid and a base portion 55(b)(ii). FIG. 8A(i) shows an embodiment may include protrusions 55p on the outer surface. FIG. 8A(ii) shows an embodiment may include a threaded surface 55(b)(iii) configured for receiving a screw or a component having external threads, roots or flanks.

FIG. 8B shows an embodiment of an inlet 101 configured as female luer component configured to couple to the male luer component shown in FIGS. 8A(i) & 8A(ii). The dotted lines in FIG. 8B outline a hollow inner channel 101(b)(i) configured to receive fluid. An embodiment of the female luer component also includes a female base portion 101(b)(ii) and a threaded cannula 101(b)(iii) configured to couple or engage the inner tubular portion 55(b)(i) of the male luer connector, which may have a complementary threaded surface 55(b)(iii).

FIG. 8C shows a transparent overlay of the male and female luer components when coupled. FIG. 8D shows the external appearance of the components when coupled, and when coupled to a hollow shaft 55. FIG. 8E shows a cross-sectional view when the components are separated, as for example in FIG. 2C or FIG. 3D.

FIGS. 8A-8E shown an embodiment of outlet 55b and inlet 101. Other embodiments need not include all features, such as a base portion or threads. A luer-slip or slip tip; duck-bill or tuohy borst valve; or other commercially available valve, or luer component may equally serve the function of transmitting fluid to an inlet. U.S. Pat. No. 8,545,479; PCT/US2002/025393; U.S. Ser. No. 11/418,838; EP/2007/0120460; U.S. Ser. No. 07/627,889 or PCT/US2005/043338, for example, illustrate other valve technologies that may serve as a male luer component, female luer component, or both.

Inlets, such as inlet 55a or inlet 101a, may be comprised of a simple fluid inlet; valve; female luer lock, as the embodiment illustrated in FIGS. 8A-8E; luer-slip or slip tip; duck-bill or tuohy borst valve; or other commercially available valve or luer component designed to receive fluid from a saline bag, syringe, fluid delivery system, or other tools in the operating room. Outlets, such as outlet 55b or outlet 55y, may be comprised of a simple fluid outlet; valve; male luer lock, as the embodiment illustrated in FIGS. 8A-8E; luer-slip or slip tip; duck-bill or tuohy borst valve; or other commercially available valve or luer component designed to deliver and/or receive fluid from a saline bag, syringe, fluid delivery system or other tools in the operating room.

Various inlets and outlets may be configured as one piece or as separate pieces coupled together. For example, as shown in FIG. 1, inlet 55a, shaft 55 and outlet 55b may be coupled or manufactured as one. As shown in FIG. 4, inlet 55a and shaft 55 may be coupled together but separate from outlet 55b, which may contain a separate inlet 55c.

A chain of inlets and outlets may be added as desired. For example, the distance between the System 1000's first proximal inlet (inlet 55a shown in FIG. 1) and the inlet 101a of contents 100 may be intermediated by multiple inlets and outlets, or male and female luer locks. FIG. 4 shows a configuration wherein the hollow shaft 55 and outlet 55b are separable pieces, so that shaft 55 includes an additional outlet 55y configured for coupling to an additional inlet 55c of the outlet 55b. In another embodiment, the hollow shaft 55 comprises largely of a chain of inlets and outlets.

Outlet 55b may be configured to receive a downward pressing force from first end 20 towards second end 30 to facilitate movement of outlet 55b from a first position adjacent to first end 20 to a second position adjacent to second end 30. To facilitate transfer of pressure, outlet 55b, or its component sidewall or proximal surface, may include a cap, piston, plate, crown or disk portion 55d, as shown in FIG. 1. The disk portion 55d may be configured to receive pressure via the shaft 55, as shown in FIG. 1. Alternatively, the disk portion may be configured to receive pressure via a separate stick, shaft or finger.

In embodiments, container 10 may be configured to store content 100 or other materials, such as bag or sheath within the tube. Content 100 may be preassembled within container 10 or inserted into the container 10 via the first proximal end 20 or second distal end 30. Content 100 may be placed within container 10 in close proximity to first proximal end 20 as shown in FIG. 4 or may be placed at a middle portion of second distal end 30, as shown in FIG. 1. Content 100 may be pushed out of the container 10 via a pressing force upon outlet surface 55c and mechanism described below, or pulled within the body of container 10 to exit through second distal end 30 of container 10 pre- or post-partial or complete inflation. Alternatively, as content 100 receives air, fluid, and/or other substances, content 100 may move, automatically fall, or be forced out of container 10 due to increase weight, gravitational force, or force applied by being inflated and/or injected.

Container 10 may be various shapes and/or sizes, wherein a length and/or wall thickness of container 10 may be pre-specified, include one or more inner cannula of varying thickness or length. The diameter of the first end 17a may be equal or different from the diameter of second end 17b. Additionally, container 10, first end 20, second end 30, shaft 55, various inlets and outlets, protrusions, and other components and elements of system 1000 may have a perimeter of alternative shapes, such as a circular, oval, rectangular, polygonal, or a trapezoidal perimeter. A perimeter of the inlets or outlets may have substantially the same shape as inner surface 11 of container 10, such that the inlets or outlets are positioned adjacent to the inner surface 11 of container 10 with a diameter less than the diameter of container 10.

To facilitate movement of the outlet portion within the body of container 10, inner surface 11 of container 10 may include guide(s), track(s), or rail(s) 19. Track 19 may be configured to interface with outlet 55b, and outlet 55b may also include balls or rollers 18 configured to interface with the track 19, in addition to stops to prevent passage of outlet 55b outside of the second end 30 of container 10.

In another embodiment, a track, rail or guide may be located on shaft 55. FIG. 12 shows an embodiment where the shaft has a rail 19. In an embodiment, container 10 may also include a disk 300 perpendicular to the vertical axis of the container. The disk 300 may comprised of an inner hole 301, with one large hole 301c configured for passing the shaft and two unequal sized holes, 301a and 301b in fluid communication with the large hole. Additionally, the shaft may include a tab 19t, such that 19t is capable of sliding through hole 301a but is too large to slide through hole 301b. In a first configuration, tab 19t is configured over placement over hole 301a. Thus, when shaft 55 is pressed down, the shaft stops when tab 91 intersects hole 301a. Conveniently, this intersection point may be positioned where protrusion 11(p) and 101(p) align. In order to move the shaft further, a practitioner would rotate the device until tip 19t intersected hole 301b. This rotation may uncouple or unscrew inlet 101 from outlet 55b. Uncoupling may be further facilitated by one or more protrusion(s) 11p on the inner surface 11s, as shown in FIG. 12A, and one or more protrusion(s) 101p on the inlet's outer surface 101s. Additionally, release content

101 may further be facilitated by a narrowed second end, wherein the diameter of the second end, 17b, is less than the diameter of the first end, less than the diameter of outlet 55b, but equal to or larger than the diameter of the inlet 101 so the inlet may be released. A narrow second end 30 has the additional benefit of limiting, reducing, or preventing the outlet 55b from exiting the second end. Alternatively, the second end 30 may have an expandable diameter.

Figure 12B:
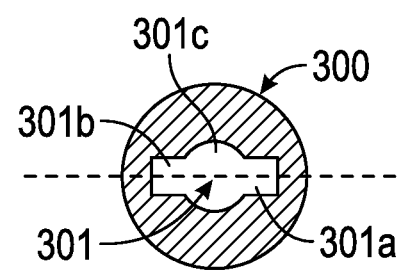
Figure 12C:
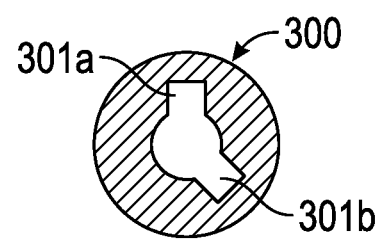

FIGS. 12B & 12C show top-down perspective of alternative embodiments of a disk. In FIG. 12A, holes 301a and 301b are symmetrically placed required a 180 degree rotation of the shaft in order for tab 19a to reach one hole or the other. In FIG. 12B, holes 301a and 301b are not symmetrically placed. Holes 301a and 301b may be positioned to require any degree of rotation.

In some embodiments, first end 20 of container 10 and second end 30 of container 10 may be configured to be open. In other embodiments, first end 20 of container 10 may be configured to be closed or covered with a hole allowing for passage of one or more shaft, conduits, cords or lumens.

Figure 13:
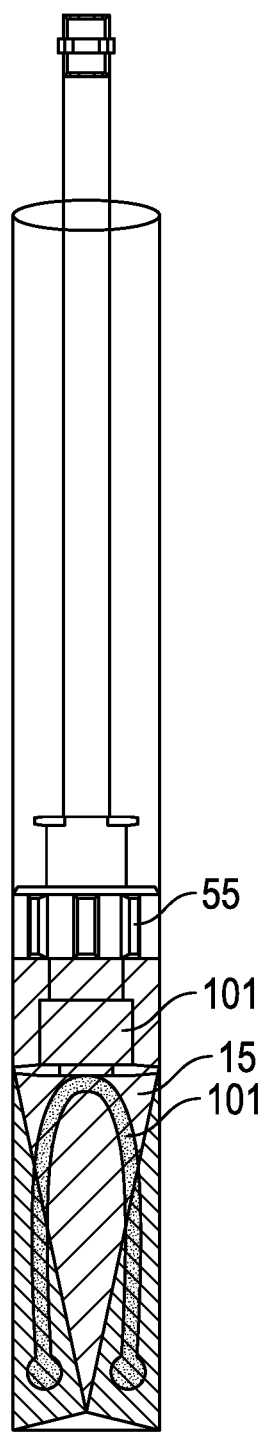
FIG. 13 shows an embodiment including a flexible seal.

FIG. 13 shows a second end 30 of container 10 configured to include a flexible seal 15 comprised of a partial seal, mouth, teeth or prongs (referred to individually and collectively hereinafter as "flexible seal 15") wherein when pressure is applied to flexible seal 15, portions of flexible seal 15 may project outward to open flexible seal 15 allowing content 100 to leave container 10.

In an embodiment, the inflatable content may be housed within the container and be adjacent to the second end which contains the teeth or prongs of a flexible seal. In another embodiment, the flexible seal may extend distally from the second end of the container so the inflatable content is housed distal to the second end (i.e. not between the first end and second end of the container). In another embodiment, pushing down the fluid outlet from the first end to the second end may not be required; instead, the inflatable content need only be inflated and released from the teeth, which opens as the content is inflated.

Flexible seal 15 may be positioned to cover second end 30, and may be configured as a delivery outlet to allow content to exit the body of container 10. Alternatively, flexible seal 15 may be positioned to cover both the first end 20 and second end 30. Hollow shaft 55 may be rigid or flexible body. A rigid shaft may facilitate dual-use of the shaft as an inlet for fluid and as a means of applying downward force upon outlet 55b to facilitate movement and delivery of content 100 out of the second end 30. A flexible shaft may permit injection of fluid but also requires application of force upon outlet 55b by other means, such as by another shaft, stick or finger.

As shown in FIG. 1, hollow shaft 55 may be affixed to outlet 55b. Alternatively, as shown in FIG. 4, hollow shaft 55 may be detachable. As shown in FIG. 5, a hollow shaft 55 may also include one or more hollow inner tubes or lumen 51.

Hollow shaft 55 may have a predetermined, fixed, or adjustable length, wherein the length of hollow shaft 55 may vary based on the length of container 10. To facilitate an adjustable length, hollow shaft 55 may include an inner and outer shaft. If coupled to a handle 50, the handle may have a button configured to adjust and lock the length of hollow shaft 55 within container 10. Responsive to the button being pressed, the length of hollow shaft 55 may be adjusted. Responsive to the button no longer being pressed, the length of hollow shaft 55 may be locked in place.

In other embodiments, outlet 55b and inlet 101 may be configured for alternative lock, twist and or release mechanisms. Alternative twist and lock mechanisms may be utilized to open and/or close inlet ports and/or outlet ports, such as first inlet port 55a, outlet port 55, and/or second inlet port 101. For example, in a first position handle 50 and/or outlet 55b may be in an open position configured to allow air, fluid, and/or other substances to move from first inlet port 55a to content 100. In a second position, handle 50 and/or outlet 55b may be in a closed position configured to prevent air, fluid, and/or other substances from moving from first inlet port 55a to content 100.

FIGS. 9A-9D show an embodiment of System 1000 including an encasement, shroud, or bag 70 with a first end 71 and a second rim end 73. Bag 70 may serve as a delivery shroud configured to protect content 100 and facilitate to movement of content 100 while being inflated and released from the container 10. Additionally, a bag 70 may prevent content 100 from sticking to inner surface 11 or breaking, tearing, ripping upon movement through container 10. Simply by pushing shaft 55, a medical practitioner may cause the encasement to unfold and deliver content 100 into a patient as described by the embodiments below.

Figure 9A:
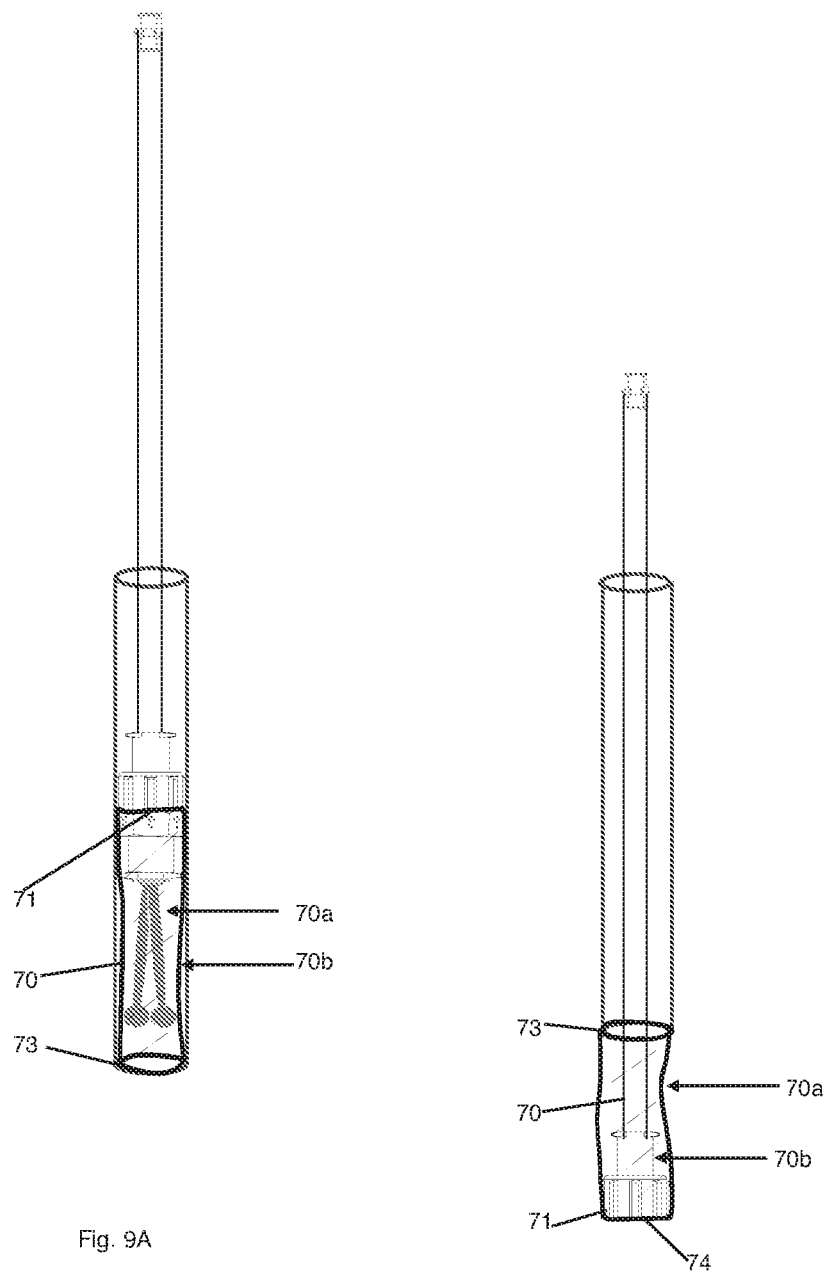
FIGS. 9A-9D show an embodiment of a surgical inflation and delivery system including an encasement.
Figure 9B:
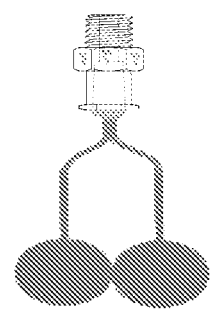

FIGS. 9A and 9B show an embodiment wherein the second rim end 73 is affixed or adhesed to, on, and/or around second end 30 of container 10. Rim end 73 may be substantially the same diameter as the second end to facilitate coupling. The figures also illustrate the first end 71 of bag 70 affixed or adhesed to on or around outlet 55b, or on the rim surface of outlet 55b in contact with inlet 101a. First end 71 may include a hole 74 configured to facilitate passage of passage of inlets and outlets, for example, outlet 55b and/or inlet 101a.

FIG. 9A and FIG. 9B show that first end 71 of bag 70 may be configured to move from a first position to a second position, respectively, while the rim end 73 remains fixed to the second end. In the first position, the first end 71 and rim end 73 are extended from outlet 55b to the second end 30 of container 10, respectively, to encase content 100. As outlet 55b pushes the first end 71 past the second end 30, the bag walls unfurl or reverse so the interior walls 70a of the bag at the first position is partially exposed to the exterior, and the exterior walls 70b of the bag at the first position is partially reversed into the interior of the bag. When the bag is 70 fully extended and reversed, as shown in FIG. 9B, outlet 55b is pressed against first end 71. In this position, the bag's walls are unfurled or reversed so the interior walls 70a of the bag at the first position are exposed to the exterior, and the exterior walls 70b of the bag at the first position are reversed into the interior of the bag. In this position, the first end 72 is distal to rim end 73, which has remained in a fixed position.

In other embodiments, first end 71 is positioned adjacent to, on or around the proximal portion of content 100. However, in this configuration, the bag is released into the patient along with the contents 100. The first end 71 or bag hole 74 may also be affixed or adhesed to outlet 55b, and/or inlet 101a.

Figure 9C:
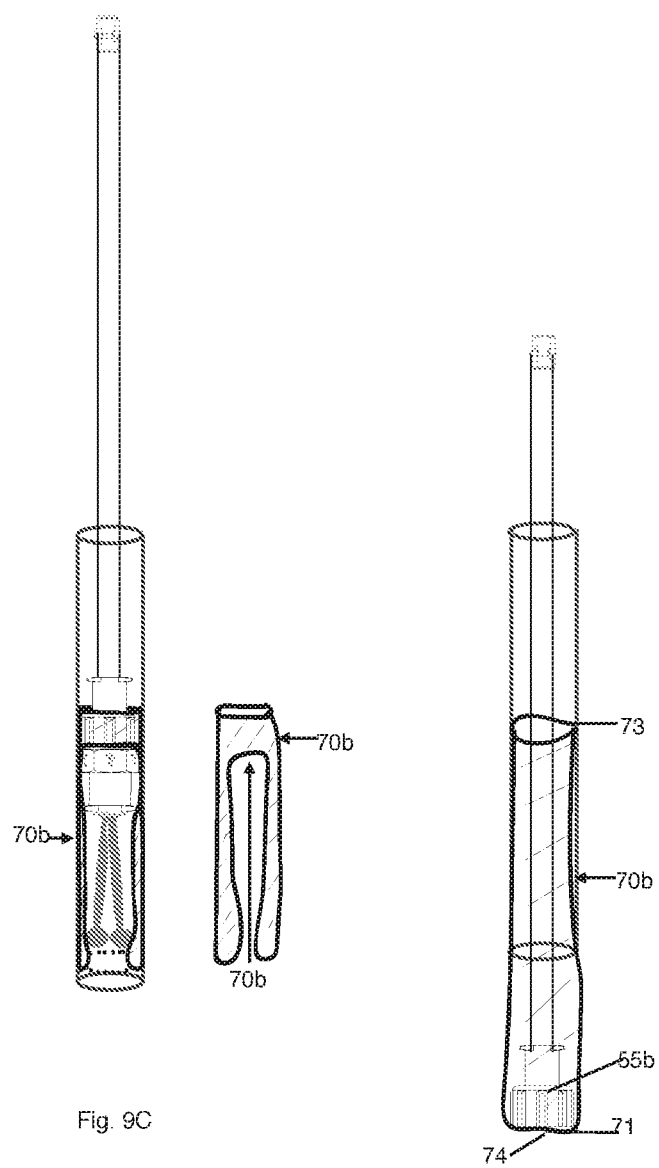
Figure 9D:
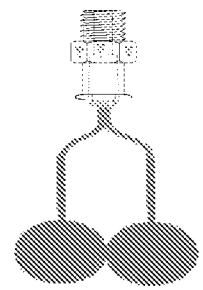

FIGS. 9C-9D show an alternative embodiment of bag 70 wherein the rim end 73 or wall of the bag is affixed, attached or adhesed to any point along the inner surface 11 of container, between the first end 20 and second end 30. First end 71 may be positioned adjacent to, on or around outlet 55b or between outlet 55b and inlet 101a. First end 71 may include a hole 74 configured to facilitate passage of passage of inlets and outlets, for example, outlet 55b and/or inlet 101a.

In the first position illustrated in FIG. 9C, the first end 71 is recessed into the bag 70, so that the walls of the bag are folded and closer to the second end of the container than first end 71 or rim end 73. In this orientation, the bag walls form a double layer to encase the contents, which are positioned into the recess of outer wall 70b. Outlet 55b may travel from the first end 20 to the second end 30 of the container 10, incrementally pushing the first end 71 away from the first end 20 of the container towards the second end 30 of the container.

FIG. 9D shows a second configuration wherein outlet 55b has pushed the first end 71 past the second end 30, the recess is eliminated, and bag 70 is fully extended. In this position, the inlet end 72 is distal to the rim end 73, which has remained in a fixed position.

In other embodiments, first end 71 is affixed, adhesed, attached or positioned adjacent to, on or around the proximal portion of content 100. However, in this configuration, the bag may be released into the patient along with the contents 100.

The embodiments illustrated have an additional benefit of preventing the outlet 55b from being delivered outside of system 1000 along with content 100. Specifically, when content 100 is released, the bag 70 enshrouds outlet 55b and prevents it from falling out of the delivery system, despite being positioned distal to the second end. This bag embodiment may obviate the need for a clip 59 of certain ridges or protrusions on the exterior surface 55c of outlet 55b.

It should be appreciated that bag 70 may be comprised of sufficient strength, stiffness, rigidity, or durability. Bag 70 may be comprised of plastic, polyurethane, nano-fibers, non-stick materials, or other biocompatible materials, and bag 70 may be configured to be scrunched, folded, or compacted.

FIGS. 10A-10D show an embodiment of System 1000 including one or more prongs 200 including a first prong end 220 and a second prong end 230. Prongs 200 may serve as a delivery shroud configured to protect content 100 and facilitate to movement of content 100 while being inflated and released from the container 10. Additionally, prongs 200 may prevent content 100 from sticking to inner surface 11 or breaking, tearing, ripping upon movement through container 10. Simply by pushing shaft 55, a medical practitioner may cause the prongs 200 to unfold and deliver content 100 into a patient as described by the embodiments below. Additionally, the prongs 200 may be released with content 100, and serves to create a perimeter around content 100, for example to create a "Y", "V", or "U" shape or other desired shape or configuration.

FIG. 10A shows an embodiment wherein prongs 200 are be positioned between the inner surface 11 and content 100 in a first position, and the first end 220 is coupled to content inlet 101. FIGS. 10B and 10C shows a second position wherein inlet 101 is positioned at the second end, and the prongs are released outside of container 10. FIG. 10D shows a fourth configuration wherein the prongs are released with content inlet 101 and content 100, and serves to create a perimeter around content 100 to create a "Y", "V", or "U" shape.

Figure 11A:
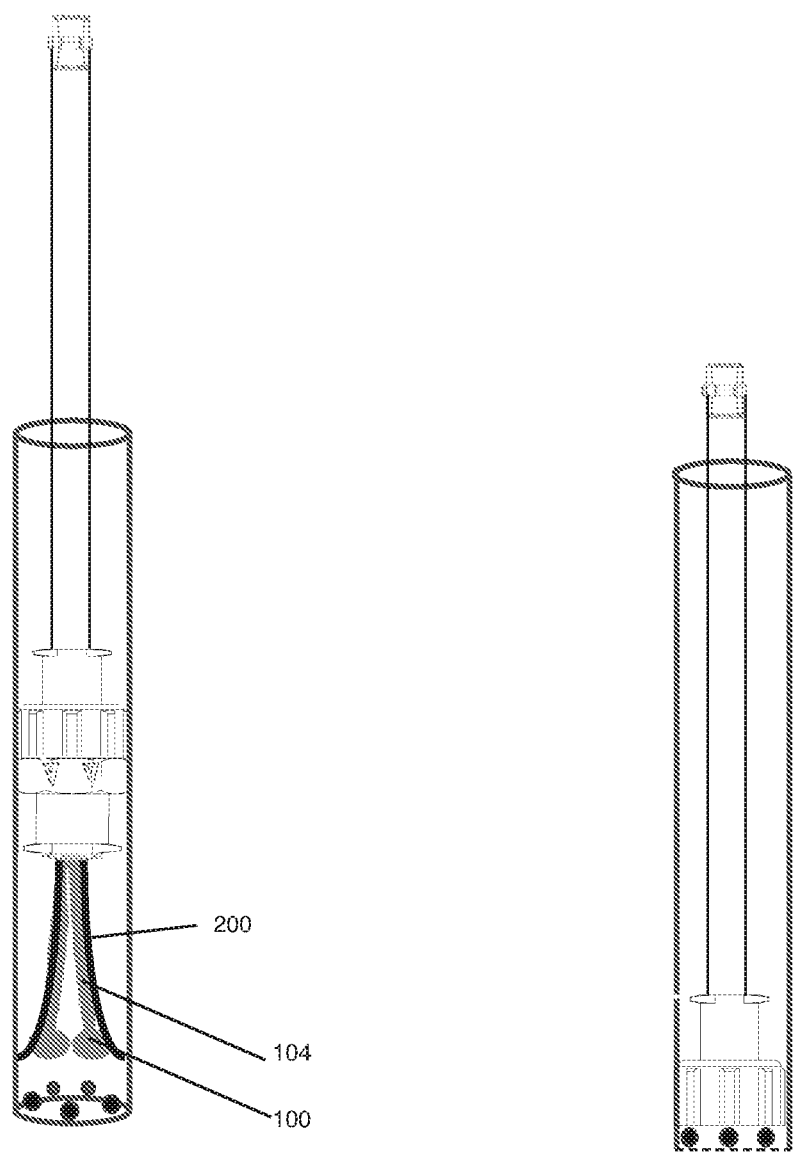
FIGS. 11A-11B show an embodiment where prongs are convex, as opposed to concave as shown in FIGS. 10A-10D.
Figure 11B:
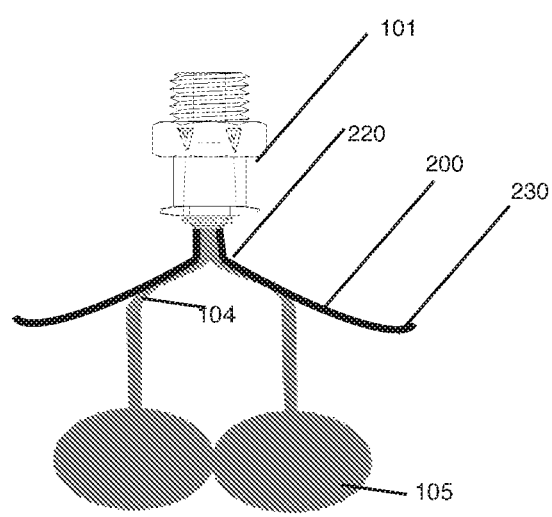

FIGS. 11A-11B show an embodiment where prongs are convex, as opposed to concave as shown in FIGS. 10A-10D. Additionally, prongs 200 may be straight without curvature, rigid, malleable, or flexible. Some portions of the prong may be curved while other portions straight, as shown in FIGS. 11A-11B. Some portions may be flexible with other portions rigid. For example, prong end 230 may be soft and malleable, whereas the arm portion of the prong is rigid. Additionally, prongs 200 may have a rectangular, trapezoidal, oval, circular, any polygonal or mixed shape. Prongs 200 may be rectangular with rounded ends, collinear tubes, or a compliant cylinder that distorts or conforms.

The total perimeter of one or more prongs may be attached, affixed or coupled to the perimeter of content 100. Alternatively, portions of prong(s) 200 may be attached, affixed or coupled to the perimeter of content 100. The distance between the first prong end 220 and second prong end 230 may be greater, equal, or lesser than the length of content 100, inlet 101, outlet 55b, container 10 or any components of system 1000.

FIGS. 11C-11D show an embodiment where the first prong end 220 is coupled to outlet 55b. First prong end 220 may be coupled or affixed to outlet 55b, container 10 or another portion of the system 1000. In this configuration, prongs 200 may be limited or prevented from being released with content 100 and achieving a desire configuration of content 100 but may serve additional manipulation functions of the outer tube in a surgical context.

When prong 200 is coupled to content 100, and content 100 include one or more balloons connected to an elongated lumen, tube or member (hereinafter "elongated member 110"), the prongs 200 may be coupled to a portion of content 100 or elongated member 104 (as shown in FIGS. 11A & 11B) to prevent an obstruction of vessels or a tourniquet effect on vital organs of the patient, such as the mesentery, bowel, or other surrounding organs. For example, if the elongated member 104 is too thin, it may cut into vessels on a vital organ when a force, such as a gravitation force, is exerted upon the content 100 (especially if inflated with fluid). Or the elongated member 104 may obstruct the flow of blood or create a tourniquet. Examples of important vessels include the aorta and common iliacs. A sufficiently thick elongated member 104 may prevent blanching of the vital tissue and tissue of nearby organs, such as mesenteric, bowel, or other human tissue.

As shown in FIGS. 11A-11B, prongs 200 may be coupled to content 100 to provide additional thickness to content 100 or elongated member 104 to prevent blanching or a tourniquet on delicate tissue or vital vessels. Content 100 may include one or more elongated members 104 coupled to one more balloons 105. Therefore, prongs 200 may be coupled to one or more inflatable balloons 105, or alternatively to an elongated member 104 to provide additional thickness to balloons 105 or elongated member 104. In some embodiments, the thickness achieved by the prongs may be 0-2 mm, 2-4 mm, 4-6 mm, 6-8 mm, 8-10 mm, 10-12 mm, 12-14 mm, 14-16 mm, or 16 mm-18 mm.

System 1000 may also facilitate inflation and delivery of the organ retractor devices, as described in the '960 application or other balloon based devices wherein the fluid amount desired to be injected is greater than 50 ml, for example between 100-200 ml, 200-300 ml, 300-400 ml, 400-500 ml, 500 ml-600 ml or even greater than 500 ml. Such balloon based devices may include one or more expandable balloon or portion, such as catheters.

Parts of the system 1000 and any content 100 may be constructed from a variety of materials, including but not limited to biocompatible materials, plastic, metal, cloth, textiles, synthetic fibers, nylon, rubber, Silicone (Polydimethylsiloxane), Polyurethane (e.g., Aliphatic Aromatic), Polycarbonate Urethane, Polyvinyl Chloride (PVC), Polyethylene Mesh or Film (e.g, LLDPE, LDPE, HDPE), Polypropylene Mesh or Film, Nylon, Pebax, Polycarbonate, or other materials with other appropriate or similar properties.

Parts of system 1000 and content 100 may have various coatings to facilitate insertion, retrieval and placement of the device into a patient. This include lubricous time release coatings, surface modifications for lubricity, hydrophilic lubricous coatings When content 100 is inflated with a fluid, the fluid may also be carbon dioxide or another gas with similar properties through surgical inflation techniques. Or it may be a magnetic fluid capable of filling all inflating members (such as the anchor(s) 12 or elongated member 14). Such a magnetic fluid could interact with magnets or electromagnets placed internally in or externally on the patient.

The fluid within content 100 may be a biocompatible fluid that meets regulatory requirements. For example, it may be water or physiologic saline, dextran, malithol or other more dense fluids than saline. Biocompatible fluids guard against adverse effects during a leak. The fluid may also be varied to have different flow rates and densities to control balloon weight, rate, position and distribution of inflation. Also, fluid variations may be employed to change or adapt the amount of weigh.

Content 100 may have a relatively distensible wall so as to allow thickening and inflation by the injection of the fluid. For example, the elongated member 14 may be constructed similar to (but larger in scale than) some angioplasty balloons or balloons used in Foley's catheter, Humi, or V-CARE instruments to stretch or unfold into desired shapes that optimize weight and positioning.

When magnets are employed in the device, for example as anchor(s) 12, the magnet could be of various types, including but not limited to Alnico, NdFeB, Ferromagnetic Alloys or similar magnets with other appropriate or similar properties.

The content inflation and delivery system and its various embodiments may be packed, sold or delivered as a kit with a surgical tool or device, including the organ retractor described in the '960 application"), or other devices that require inflation by a fluid, such as a catheter or other balloon based devices. In addition, one or more devices may be sold in a system kit. For example, such a kit may include one or more organ retractors. The device may come pre-assembled or separately with the system. The kit may include other materials including appropriate labeling, one or more sterile barriers (e.g., 1, 2, or 3 or ore barriers), trays, bags, and a box. These other components may be sterile.

System 1000 may be used with a variety of medical devices, including the organ retractor described in U.S. Pat. App. Publication No. 2012/13432960 entitled ORGAN RETRACTOR filed on Mar. 28, 2012 ("the '960 application"). The '960 application shares a common inventor with the present application and discloses an organ retractor for facilitating positioning of a mesentery or organs connected to a mesentery within an abdominal cavity of a patient.

In a minimally invasive surgical context, the content delivery and inflation system may have the following dimensions and characteristics. The container (diameters 17a and 17b) may be 2 to 20 mm wide. The container or distance between the first end 20 and second end 30 may be up to 50 cm long, depending on the size of the inflatable content, whether it is used in a laparoscopic or robotic context, and the intended location (e.g., abdomen with a larger depth or hand with a small depth). The length of the shaft may be up to 60 cm long. The diameter of the shaft may be up to 20 mm wide. An individual prong may be up to 40 cm long, depending on the context. These dimensions may be larger in an ordinary surgical context, or even in a minimally invasive context. In a laparoscopic embodiment, the length of the container is 20-40 cm, the length of the shaft is 25 cm to 45 mm long, the diameter of the container is 5-10 mm, and the diameter of the shaft is 4-8 mm, and the length of the prong is 5-15 cm.

System 1000 may also facilitate inflation and delivery of the organ retractor devices, as described in the '960 application or other balloon based devices wherein the fluid amount desired to be injected is greater than 50 ml, for example between 100-200 ml, 200-300 ml, 300-400 ml, 400-500, ml or even greater than 500 ml. Such balloon based devices may include one or more expandable balloon or portion, such as catheters.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

Reference throughout this specification to "an embodiment", "an embodiment", "one example" or "an example" means that a particular feature, structure or characteristic described in connection with the embodiment or example is included in at least an embodiment of the present invention. Thus, appearances of the phrases "in an embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

Various examples of embodiments are now discussed.

Embodiments disclosed herein describe a content inflation and delivery system. The content inflation and delivery system may include a container including (a)(i) a first end with a first end diameter and a second end with a second end diameter, (a)(ii) an inner surface and an outer surface, and (a)(iii) a vertical axis between the first end and the second end. The container may also include a hollow shaft including (a)(i) a first shaft end comprising a fluid inlet configured to receive a fluid and (a)(ii) a second shaft end configured to deliver the fluid, wherein the hollow shaft may be movable through the container along the vertical axis; and wherein the first shaft end may be farther from the second end of the container than the second shaft end. The container may also include a fluid outlet comprising or coupled to the second shaft end, the fluid outlet being comprised of a male luer connector having (a)(i) an outlet base portion with an outlet outer surface and an outlet base diameter, and (a)(ii) an inner tubular portion with a threaded inner surface and an inner diameter, wherein the inner diameter may be smaller than the base diameter; and the base diameter may be smaller than the first end diameter and the second end diameter. The container may also include an inflatable content comprising one or more of an inflatable balloon configured for coupling to a balloon inlet, the balloon inlet being comprised of a female luer connector having (a)(i) an inlet base portion with an inlet outer surface and an inlet base diameter; and (a)(ii) a threaded cannula configured to couple or engage the inner tubular portion of the male luer connector In embodiments, in a first configuration the inflatable content may be in fluid communication with the fluid outlet and the hollow shaft; the female luer connector may be coupled to the male luer connector; the outlet base portion may be located between the first end and the second of the container; the outlet base portion may be closer to the first end than the inlet base portion; and a content diameter of the inflatable content may be less than the second end diameter and less than the first end diameter of the container;

In embodiments, in a second configuration the balloon inlet may be uncoupled from the second shaft end; the female luer connector may be uncoupled from the male luer connector; the outlet base portion may be located between the first end and the second of the container; the outlet base portion may be closer to the first end than the inlet base portion; and a content diameter of the inflatable content may be greater than the second end diameter and greater than the first end diameter of the container.

In embodiments, the inflatable content may comprise a first balloon and a second balloon connected by a conduit, wherein each balloon may be configured to receive 100 ml to 500 ml of fluid.

Embodiments may include a plurality of container protrusions located on the inner surface of the container and a plurality of balloon inlet protrusions located on the inlet outer surface. The plurality of container protrusions may include a first container protrusion and a second container protrusion, and the plurality of balloon inlet protrusions may include a first balloon inlet protrusion. The first balloon inlet protrusion may be configured to slide between the first container protrusion and the second container protrusion, and to position adjacent to the first container protrusion and the second container protrusion. The plurality of container protrusions and the plurality balloon inlet protrusions may be configured to limit rotation of the balloon inlet in a direction perpendicular to the vertical axis.

Embodiments may comprise (i) a first prong coupled to a first portion of the conduit between the balloon inlet and the first balloon, and (ii) a second prong coupled to a second portion of the conduit between the balloon inlet and the second balloon. In embodiments the first prong, second prong, first balloon, and second balloon may be configured to create a Y, U or V shape.

Embodiments may include (1) a container including (a)(i) a first end with a first end diameter and a second end with a second end diameter, (a)(ii) a container protrusion positioned on an inner surface of the container between the first end and second end, and (a)(iii) a vertical axis between the first end and the second end. Embodiments may also include (2) a fluid inlet and a fluid outlet; wherein the fluid outlet may be positioned between the fluid inlet and the second end; the fluid outlet may be in fluid communication with the fluid inlet; and the fluid outlet may be movable between the first end and the second end. Embodiments may also include (3) an inflatable content configured to be housed within the container; wherein the inflatable content may be configured to move between the first end and the second end; and the inflatable content may be positioned between the fluid outlet and the second end. Embodiments may also include (4) a content inlet including an outer surface, the outer surface including a content inlet protrusion; wherein the content inlet may be configured to couple to the fluid outlet and receive a fluid from the fluid outlet; content inlet may be coupled to the inflatable content and may be configured for delivering the fluid into the inflatable content; and the content inlet protrusion may be configured to interface with the container protrusion to limit rotation of the content inlet in a direction perpendicular to the vertical axis between the first end and the second end.

Embodiments may include a hollow shaft configured to couple to the fluid inlet, wherein the hollow shaft may be configured to be in fluid communication with the fluid outlet and the content inlet.

In embodiments, the hollow shaft may include a detachable clamp configured to snap onto the hollow shaft, having a clamp diameter greater than the first end diameter. The detachable clamp may have a proximal snap point and a distal snap point, the proximal snap point being farther from the second end than the first snap point; wherein the detachable clamp may limit movement of the shaft from the first end to the second end, along the vertical axis from the second snap point to the first snap point, and any portion of the shaft proximal to the first snap point.

In embodiments, an outer outlet surface of the fluid outlet may include an outlet protrusion along a same axis of the container protrusion, wherein the container protrusion may be configured to limit movement of the outlet beyond a point of intersection between the outlet protrusion and container protrusion.

Embodiments may include a plurality of container protrusions and a plurality of container inlet protrusions.

In embodiments, the plurality of container protrusions may include a first container protrusion and a second container protrusion, and the plurality of container inlet protrusions including a first container inlet protrusion; wherein the first container inlet protrusion may be configured to move between the first container protrusion and the second container protrusion, and may also be configured to position adjacent to the first container protrusion and the second container protrusion.

In embodiments, the plurality of container protrusions and the plurality content inlet protrusions may be configured to limit rotation of the content inlet in a direction perpendicular to the vertical axis.

In embodiments, the fluid outlet may be comprised of a male luer connector and the content inlet being comprised of a female luer connection configured for coupling to the male luer connection.

In embodiments, the male luer connector may include (a)(i) an outlet base portion with an outlet outer surface, and (a)(ii) an inner tubular portion with a threaded inner surface and an inner diameter; wherein the inner diameter may be smaller than the base diameter; and the base diameter may be smaller than the first end diameter and the second end diameter. In embodiments the female luer connector may include (b)(i) an inlet base portion with an inlet base diameter; and (b)(ii) a threaded cannula configured to couple or engage the inner tubular portion of the male luer connector.

In embodiments, the fluid outlet and fluid inlet may include one or more a valve and may be configured for coupling via a screw mechanism.

In embodiments, the inflatable content may comprise a first balloon and a second balloon connected by a conduit; wherein each balloon may be configured to receive 100 ml to 500 ml of fluid.

Embodiments may include a hollow lumen with a lumen inlet and a lumen outlet may be affixed to the fluid inlet; wherein the hollow lumen travels through the fluid outlet and the hollow shaft; and wherein the lumen inlet may be proximal to the first end.

Embodiments may include a track disposed on the inner surface of the container; wherein the shaft or fluid outlet may include a tab configured to slide within the track.

In embodiments, the content inlet and fluid outlet may be configured to interface with each other to form a release mechanism; wherein responsive to the hollow shaft being rotated, the content inlet may be released from the fluid outlet and the content inflation and delivery system.

Embodiments may include a bag configured to encase the inflatable content while the inflatable content may be positioned within the container, the bag including a rim end and an outlet end, wherein the rim end may open and couple to an inner surface of the container, and the outlet end may be coupled to the fluid outlet. In embodiments, the outlet end may include a hole, the hole having a perimeter to encircle the fluid outlet.

Embodiments may include an inflation and delivery method comprising housing an inflatable content within a container. In embodiments the inflatable content may include (a)(i) a content inlet with an outer surface, (a)(ii) the outer surface including one or more of a content inlet protrusion; (b) the container comprised of (b)(i) a first end with a first diameter, a second end with a second diameter, and a vertical axis between the first end and second end, (b)(ii) one or more of a container protrusion on an inner surface of the container, (b)(iii) a fluid outlet positioned between the first end and the second end, and movable along the vertical axis; (c) a hollow shaft comprised of a first shaft end and a second shaft end; (c)(i) the first shaft end including a shaft inlet; and (c)(ii) the second shaft end being coupled to the fluid outlet; (d) a clamp placed a portion of the shaft proximal to the first end of the container; wherein the shaft, fluid inlet, fluid outlet and content inlet may be in fluid communication with each other and the first shaft end may be positioned proximal to the first end of the container.

In embodiments, the method may include inserting the container into a port, an incision or any desired location for delivery of the inflatable content.

In embodiments the method may include applying a first force on the fluid outlet to push the inflatable content distal to the second end.

In embodiments the method may include delivering a fluid into the shaft inlet and inflating the inflatable content.

In embodiments the method may include rotating the shaft to cause the content inlet protrusion to interface with the container protrusion.

In embodiments the method may include pulling the fluid outlet from the second end towards the first end, thereby causing the fluid outlet to uncouple from the content inlet.

In embodiments the method may include optionally pushing the shaft from the first end towards the second end to push the content inlet out of the second end and release the inflatable content from the inflation and delivery system.

In embodiments, a balloon inlet protrusion may be positioned on the inlet outer surface, and a container protrusion may be positioned on the inner surface of the container; wherein the balloon inlet protrusion may be configured to interface with the container protrusion to limit rotation of the balloon inlet in a direction perpendicular to the vertical axis.

In embodiments, the outlet outer surface may include an outlet protrusion along a same axis of the container protrusion; and wherein the container protrusion may be configured to limit movement of the fluid outlet beyond a point of intersection between the outlet protrusion and the container protrusion.

In embodiments, the hollow shaft may include a clamp configured to snap onto the hollow shaft, having a clamp diameter greater than the first end diameter; wherein the clamp may have a proximal snap point and a distal snap point, the proximal snap point being farther from the second end than the first snap point; wherein the clamp may limit the movement of the shaft along the vertical axis from the second snap point to the first snap point and any portion of the shaft proximal to the first snap point.

In embodiments, the clamp or a clip may be detachable.

In embodiments, the fluid outlet and the balloon inlet may include one or more of a valve and may be configured for coupling via a screw mechanism.

In embodiments, a hollow lumen with a lumen inlet and a lumen outlet may be coupled to the balloon inlet in the second configuration.

In embodiments, the hollow lumen may travel through the fluid outlet and the hollow shaft; and wherein the lumen inlet may be proximal to the first end.

In embodiments, the thickness of the prong and elongated member may be sufficiently large to prevent a tourniquet effect on vessels or blanching of human tissue.

Embodiments may include a handle integral with the hollow shaft and a handle outer surface, wherein the fluid inlet may be located on the handle outer surface.

Embodiments may include a track on the inner surface of the container, wherein the track may be configured to guide movement of the fluid outlet within the container; and wherein the fluid outlet may include a ridge or tab configured to slide within the track.

In embodiments, the second end of the container may include a flexible seal comprised of a plurality of teeth, the flexible seal being configured to confine the inflatable content within the container until ample force may be applied to the flexible seal to push the content through the plurality of teeth.

Embodiments may include a bag configured to encase the inflatable content while the inflatable content may be positioned within the container, the bag including a rim end and an outlet end; wherein the rim end may be open and coupled to an inner surface of the container, and the outlet end may couple to the fluid outlet.

In embodiments, the first configuration the bag may be proximate to the second end of the container, and in the second configuration a portion of the bag may be distal to the second end.

In embodiments, the outlet end may include a hole, the hole having a perimeter to encircle the fluid outlet; and wherein in the second configuration the outlet end may be distal to the second end.

In embodiments, the bag may form a recessed portion with a double wall, wherein the content may be configured to be positioned within the recessed portion.

In embodiments, the balloon inlet and fluid outlet may be configured to interface with each other to form a locking mechanism; wherein responsive to the hollow shaft being rotated, the balloon inlet and the fluid outlet may be in an open or a closed position; wherein in the closed position, air or fluid may not exit the balloon inlet into the fluid outlet; and wherein in the open position, air or fluid may exit the balloon inlet into the fluid outlet.

In embodiments, the balloon inlet and fluid outlet may be configured to interface with each other to form a release mechanism; wherein responsive to the hollow shaft being rotated, the balloon inlet may be released from the fluid outlet and the content inflation and delivery system.

In embodiments, one or more of a prong may be affixed or coupled to the content inlet, such that a portion of the inflatable content may be coupled to the prong, and may be configured to create a Y, U or V shape when the inflatable content may be released from the content and inflation delivery system.

In embodiments, a thickness of the prong and inflatable content may be sufficiently large to prevent a tourniquet effect on vessels or blanching of human tissue.

Embodiments may include a handle integral with the hollow shaft and a handle outer surface, wherein the fluid inlet may be located on the handle outer surface.

In embodiments, the second end of the container may include a flexible seal comprised of a plurality of teeth, the flexible seal being configured to confine the inflatable content within the container until ample force may be applied to the flexible seal to push the inflatable content through the plurality of teeth.

In embodiments, the bag may form a recessed portion with a double wall, wherein the content may be configured to be positioned within the recessed portion.

In embodiments, the content inlet and fluid outlet may be configured to interface with each other to form a locking mechanism; wherein responsive to the hollow shaft being rotated, the content inlet and the fluid outlet may be in an open or a closed position; wherein in the closed position, air or fluid may not exit the content inlet into the fluid outlet; and wherein in the open position, air or fluid may exit the content inlet into the fluid outlet.

Embodiments may include an inflation and delivery method. The method may include housing an inflatable content within a container (a) the inflatable content including a content inlet, and (b) the container comprised of (b)(i) a first end with a first diameter, a second end with a second diameter, and a vertical axis between the first end and the second end (b)(ii) a fluid inlet coupled to a fluid outlet, the fluid outlet being positioned between the first end and the second end, and being movable along a vertical axis between the first and second end; wherein in a first configuration the fluid inlet, the fluid outlet and content inlet may be in fluid communication.

The method may also include inserting the container into a port, an incision or any desired location for delivery of the inflatable content.

The method may also include applying a first force on the fluid outlet to push the inflatable content distal to the second end.

The method may also include delivering a fluid into the fluid inlet and inflating the inflatable content.

The method may also include releasing the inflatable content from the outlet.

In embodiments, the container may include one or more of a container protrusion on an inner surface of the container between the first end and the second end; the content inlet having an outer surface, the outer surface including a content inlet protrusion; wherein rotating the fluid outlet causes the content inlet protrusion to interface with the content outlet protrusion, such that rotation of the content inlet may be limited in a direction perpendicular to the vertical axis; wherein rotation and pulling the fluid outlet from the second end towards the first end causes the fluid outlet to uncouple from the content inlet.

Embodiments may include a hollow shaft that may be coupled to the fluid inlet to facilitate delivery of fluid, movement of the fluid outlet along the vertical axis, and rotation of the fluid outlet.

In embodiments, a clip or clamp may be placed on the shaft prior to applying the first force on the fluid outlet, and wherein the clip or clamp may be detached from the shaft after inflation.

In embodiments, after inflation, a second force may be applied to the shaft to push it from the first end towards the second end sufficient to push the content inlet out of the system.

In embodiments, the outlet protrusion may be located on a distal end of the fluid outlet.

In embodiments, the outlet protrusion may be located on a proximal end of the fluid outlet.

What is claimed is:

1. A content inflation and delivery system comprising:
   a container including (a)(i) a first end with a first end diameter and a second end with a second end diameter, (a)(ii) an inner surface and an outer surface, and (a)(iii) a vertical axis between the first end and the second end;
   a hollow shaft including (a)(i) a first shaft end comprising a fluid inlet configured to receive a fluid and (a)(ii) a second shaft end configured to deliver the fluid;
   wherein the hollow shaft is movable through the container along the vertical axis;
   a fluid outlet comprising or coupled to the second shaft end;
   a content inlet;
   an inflatable content, a proximal end of the inflatable content being coupled to a distal end of the content inlet, the content inlet including a proximal end that is selectively coupled to the second shaft end, the proximal end of the content inlet being positioned more proximate to the first end of the container than the distal end of the content inlet, wherein a body of the content inlet has a body diameter and the distal end of the content inlet having a distal end diameter, the distal end diameter being smaller than the body diameter;
   wherein the content inlet has an outer surface, the outer surface of the content inlet being configured to be positioned directly adjacent to the container while the inflatable content moves between the first end and the second end of the container; and
   wherein the inflatable content is in fluid communication with the fluid outlet and the hollow shaft, the proximal end of the inflatable content having a diameter that is smaller than a proximal end diameter of the content inlet;
   a clip positioned on the hollow shaft configured to limit the movement of the hollow shaft within the container, the clip having a clip diameter that is larger than the first end diameter of the container, the clip always being proximal to the container's first end.

2. A content inflation and delivery system of claim 1, wherein the inflatable content comprises a first balloon and a second balloon connected by a conduit.

3. The content inflation and delivery system of claim 2, comprising (i) a first prong coupled to a first portion of the conduit between the content inlet and the first balloon, and (ii) a second prong coupled to a second portion of the conduit between the content inlet and the second balloon;
   wherein the first prong and second prong are configured to create a Y, U or V shape.

4. The content inflation and delivery system of claim 1, including a first container protrusion located on the inner surface of the container and a first content inlet protrusion located on the content inlet's outer surface.

5. The content inflation and delivery system of claim 1, further comprising a plurality of container protrusions located on the inner surface of the container and a plurality of content inlet protrusions located on the content inlet's outer surface;

wherein the plurality of container protrusions includes a first container protrusion and a second container protrusion, and the plurality of content inlet protrusions includes a first content inlet protrusion;
wherein the first content inlet protrusion is configured to be positioned adjacent to the first container protrusion and the second container protrusion;
and wherein the plurality of container protrusions and the plurality of content inlet protrusions are configured to limit rotation of the content inlet.

6. The content inflation and delivery system of claim 1, wherein the content inlet includes a valve and is configured for coupling to the fluid outlet.

7. A content inflation and delivery system of claim 1, the fluid outlet being comprised of a male luer and the content inlet being comprised of a female luer configured for coupling to the male luer.

8. A content inflation and delivery system of claim 7, the male luer including (a)(i) an outlet base portion with an outlet outer surface, and (a)(ii) an inner tubular portion with a threaded inner surface and an inner diameter;
wherein the inner diameter is smaller than a base diameter; and the base diameter is smaller than the first end diameter and the second end diameter; and
the female luer including (b)(i) an inlet base portion with an inlet base diameter; and (b)(ii) a threaded cannula configured to couple or engage the inner tubular portion of the male luer.

9. The content inflation and delivery system of claim 1, further comprising a hollow lumen with a lumen inlet and a lumen outlet;
wherein the hollow lumen travels through the hollow shaft; and
wherein the lumen inlet is proximal to the first end.

10. The content inflation and delivery system of claim 1, including a track disposed on the inner surface of the container; wherein the shaft or fluid outlet includes a tab configured to slide within the track.

11. The content inflation and delivery system of claim 1, wherein the content inlet and fluid outlet are configured to interface with each other to form a release mechanism;
wherein responsive to the hollow shaft being rotated, the content inlet is released from the fluid outlet.

12. The content inflation and delivery system of claim 1, further comprising a bag configured to encase the inflatable content, the bag including a rim end and an outlet end;
wherein the rim end is open and coupled to the container's inner surface.

13. A content inflation and delivery system comprising:
(1) a container including (a)(i) a first end with a first end diameter and a second end with a second end diameter, (a)(ii) an inner surface and an outer surface, and (a)(iii) a vertical axis between the first end and the second end;
(2) a fluid inlet and a fluid outlet;
wherein the fluid outlet is positioned between the fluid inlet and the second end; the fluid outlet is in fluid communication with the fluid inlet; and the fluid outlet is movable between the first end and the second end;
(3) an inflatable content configured to be housed within the container;
wherein the inflatable content is configured to move between the first end and the second end; and the inflatable content is positioned between the fluid outlet and the second end;
(4) a content inlet including an outer surface; wherein a proximal end of the content inlet is configured to be removably coupled to the fluid outlet and receive a fluid from the fluid outlet; and a distal end of the content inlet is coupled to a proximal end of the inflatable content, the proximal end of the content inlet being positioned more proximate to the first end of the container than the distal end of the content inlet, and the distal end of the content inlet is configured for delivering the fluid into the inflatable content, the proximal end of the content inlet having a body diameter and the distal end of the content inlet having a distal end diameter, the outer surface of the content inlet configured to be positioned directly adjacent to the container while the inflatable content moves between the first end and the second end, the proximal end of the inflatable content having a diameter that is smaller than the body diameter; and
a clip positioned on the hollow shaft configured to limit the movement of the hollow shaft within the container, the clip having a clip diameter that is larger than the first end diameter of the container, the clip always being proximal to the container's first end.

14. The content inflation and delivery system of claim 13, including one or more container protrusion(s) positioned on the inner surface of the container between the first end and second end, and the outer surface of the content inlet including one or more content inlet protrusion(s);
wherein one or more content inlet protrusion(s) are configured to be positioned adjacent to one or more container protrusion(s);
and wherein one or more container protrusion(s) and one or more content inlet protrusion(s) are configured to limit rotation of the content inlet.

15. The content inflation and delivery system of claim 13, including a hollow shaft configured to couple to the fluid inlet.

16. The content inflation and delivery system of claim 15, further comprised of a hollow lumen with a lumen inlet and a lumen outlet;
wherein the hollow lumen travels through the fluid outlet and the hollow shaft;
and wherein the lumen inlet is proximal to the first end.

17. A content inflation and delivery system of claim 13, the fluid outlet being comprised of a male luer connector and the content inlet being comprised of a female luer connector configured for coupling to the male luer connector;
the male luer connector including (a)(i) an outlet base portion with an outlet outer surface, and (a)(ii) an inner tubular portion with a threaded inner surface and an inner diameter; wherein the inner diameter is smaller than a base diameter; and the base diameter is smaller than the first end diameter and the second end diameter; and
the female luer connector including (b)(i) an inlet base portion with an inlet base diameter; and (b)(ii) a threaded cannula configured to couple or engage the inner tubular portion of the male luer connector.

18. A content inflation and delivery system of claim 13, wherein the inflatable content comprises a first balloon and a second balloon connected by a conduit.

19. The content inflation and delivery system of claim 18, comprising (i) a first prong coupled to a first portion of the conduit between the content inlet and the first balloon, and (ii) a second prong coupled to a second portion of the conduit between the content inlet and the second balloon;
wherein the first prong and second prong are configured to create a Y, U or V shape.

20. The content inflation and delivery system of claim 13, further comprising a bag configured to encase the inflatable content, the bag including a rim end and an outlet end;
   wherein the rim end is open and coupled to the inner surface of the container.

* * * * *